United States Patent

Kirkman

[11] Patent Number: 6,071,263
[45] Date of Patent: *Jun. 6, 2000

[54] APPARATUS AND METHOD FOR RETAINING A CATHETER IN A BLOOD VESSEL IN A FIXED POSITION

[76] Inventor: Thomas R. Kirkman, 14716 NE. 87th St., Redmond, Wash. 98052

[*] Notice: This patent is subject to a terminal disclaimer.

[21] Appl. No.: 08/473,129

[22] Filed: Jun. 7, 1995

Related U.S. Application Data

[63] Continuation of application No. 08/137,619, Oct. 15, 1993, Pat. No. 5,509,900, which is a continuation-in-part of application No. 07/844,715, Mar. 2, 1992, abandoned.

[51] Int. Cl.⁷ .................................................. A61M 29/00

[52] U.S. Cl. ........................ 604/104; 604/107; 604/523; 606/198

[58] Field of Search ...................... 604/104–107, 604/280, 282, 160, 174, 175; 606/198–200, 108, 191

[56] References Cited

U.S. PATENT DOCUMENTS

| | | | |
|---|---|---|---|
| 2,541,691 | 2/1951 | Eicher | 27/24 |
| 2,701,559 | 2/1955 | Cooper | 128/2 |
| 3,108,595 | 10/1963 | Overment | 128/350 |
| 3,866,599 | 2/1975 | Johnson | 128/2 L |
| 4,425,908 | 1/1984 | Simon | 128/1 R |
| 4,434,797 | 3/1984 | Silander | 128/343 |
| 4,643,184 | 2/1987 | Mobin-Uddin | 606/198 X |
| 4,654,028 | 3/1987 | Suma | 604/106 |
| 4,733,669 | 3/1988 | Segal | 128/663 |
| 4,800,882 | 1/1989 | Gianturco | 128/343 |
| 4,813,930 | 3/1989 | Elliott | 604/53 |
| 4,909,789 | 3/1990 | Taguchi et al. | 604/107 |
| 4,921,484 | 5/1990 | Hillstead | 604/104 |
| 4,936,823 | 6/1990 | Colvin et al. | 600/7 |
| 4,944,745 | 7/1990 | Sogard et al. | 606/194 |
| 4,957,484 | 9/1990 | Murtfeldt | 604/53 |
| 4,990,156 | 2/1991 | Lefebvre | 606/200 |
| 5,041,093 | 8/1991 | Chu | 604/104 |
| 5,053,008 | 10/1991 | Bajaj | 604/104 |
| 5,112,347 | 5/1992 | Taheri | 606/200 |

(List continued on next page.)

FOREIGN PATENT DOCUMENTS

| | | | |
|---|---|---|---|
| 0364293 | 4/1990 | European Pat. Off. | A61M 1/10 |
| WO 89/00834 | 2/1989 | WIPO | A61B 17/22 |
| WO93/06885 | 4/1993 | WIPO | A61M 29/00 |

OTHER PUBLICATIONS

Product Brochure, Gianturco–Rosch Billary Z–Stents, Cook Incorporated, Copyright 1989.
Product Brochure, Hickman Hemodialysis/Plasmopheresis Catheter, Davol, Inc., date unknown.
Pieper, Registration of Phasic Changes of Blood Flow by Means of a Catheter–type Flowmeter, The Review of Scientific Instruments, vol. 29, No. 11, Nov. 1958, p. 965.
Teitelbaum et al., MR Imaging Artifacts, Ferromagnetism, and Magnetic Torque of Intravascular Filters, Stents, and Coils, Radiology, vol. 166 No. 3, Mar. 1988, pp. 657–664.
Yeh et al., Blood compatibility of surfaces modified by plasma polymerization, Journal of Biomedical Materials Research, vol. 22, 1988, pp. 795–818.

*Primary Examiner*—Corrine McDermott
*Attorney, Agent, or Firm*—David V. Carlson; Seed IP Law Group PLLC

[57] ABSTRACT

A method and apparatus for retaining a catheter tip in a fixed position within a blood flow and preventing it from contacting a blood vessel wall. The apparatus includes a tip retainer at the distal end of the catheter that anchors the tip of the catheter within the blood vessel. The catheter tip is retained within the blood vessel spaced from the wall to ensure that it does not contact the wall of the blood vessel. This reduces damage to the blood vessel caused by chronic movement and contact between the catheter tip and the wall of the blood vessel. In one embodiment, the tip retainer includes a prong that penetrates the wall of the blood vessel, thus preventing the catheter tip from moving longitudinally within the blood vessel. In alternative embodiments, the tip retainer contacts the wall but does not penetrate the wall.

17 Claims, 17 Drawing Sheets

U.S. PATENT DOCUMENTS

| | | | |
|---|---|---|---|
| 5,122,125 | 6/1992 | Deuss | 604/282 |
| 5,135,517 | 8/1992 | McCoy | 604/281 |
| 5,152,777 | 10/1992 | Goldberg et al. | 606/200 |
| 5,167,634 | 12/1992 | Corrigan, Jr. et al. | 604/160 |
| 5,180,368 | 1/1993 | Garrison | 604/104 |
| 5,256,146 | 10/1993 | Ensminger et al. | 604/104 |
| 5,267,960 | 12/1993 | Hayman et al. | 604/106 |
| 5,275,610 | 1/1994 | Eberbach | 606/198 |

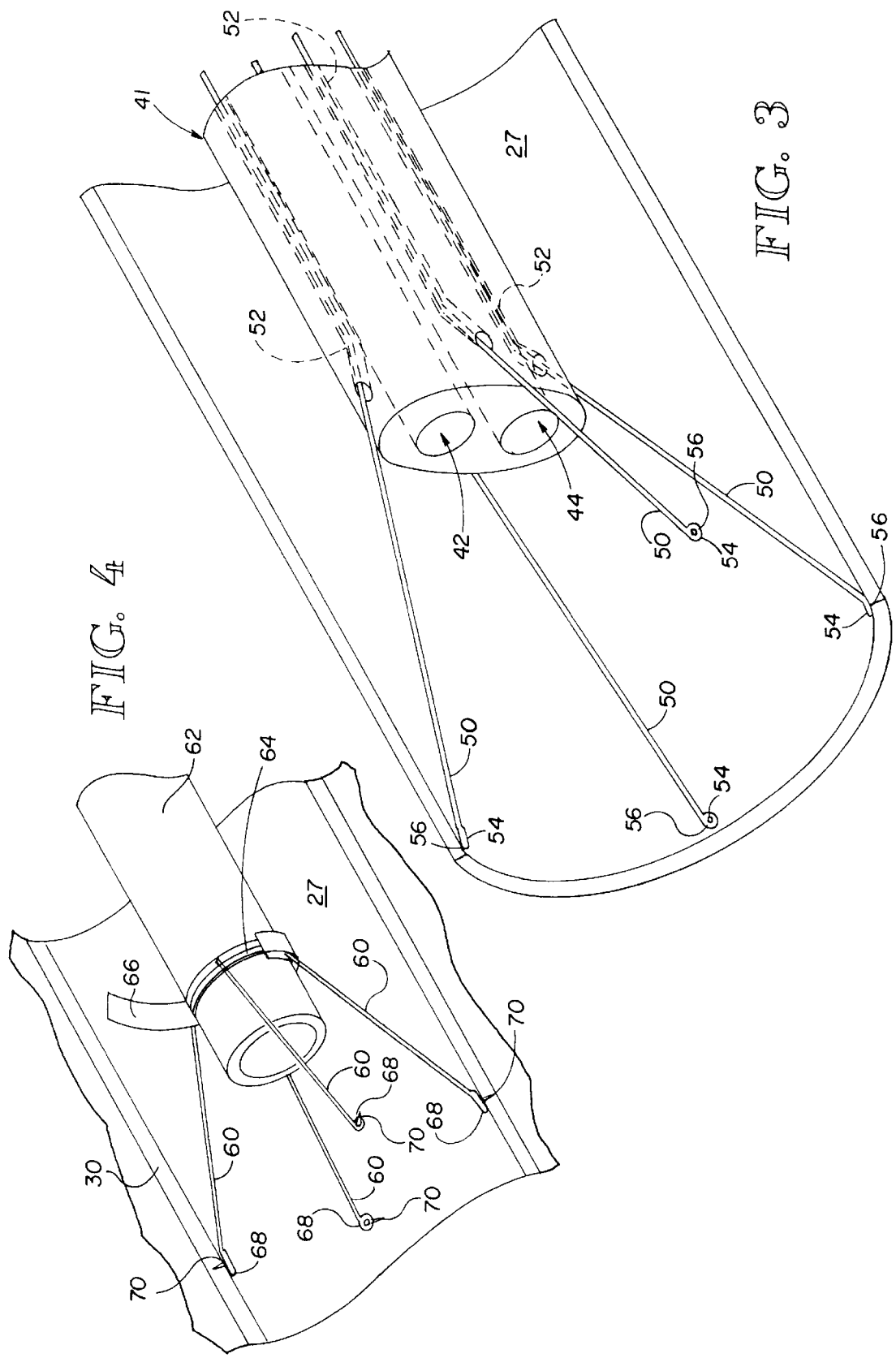

FIG. 12
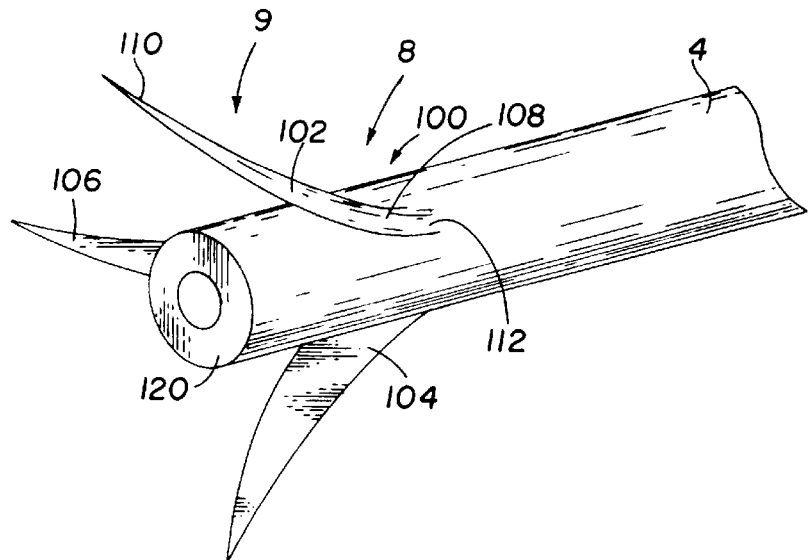
FIG. 13
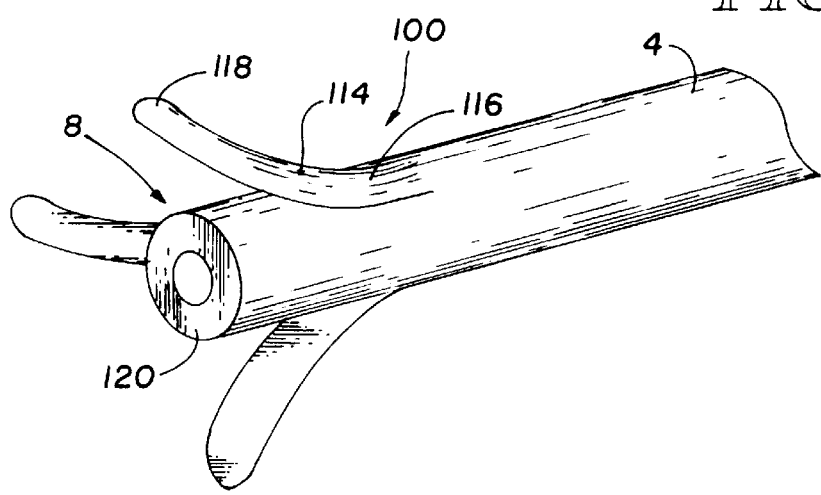
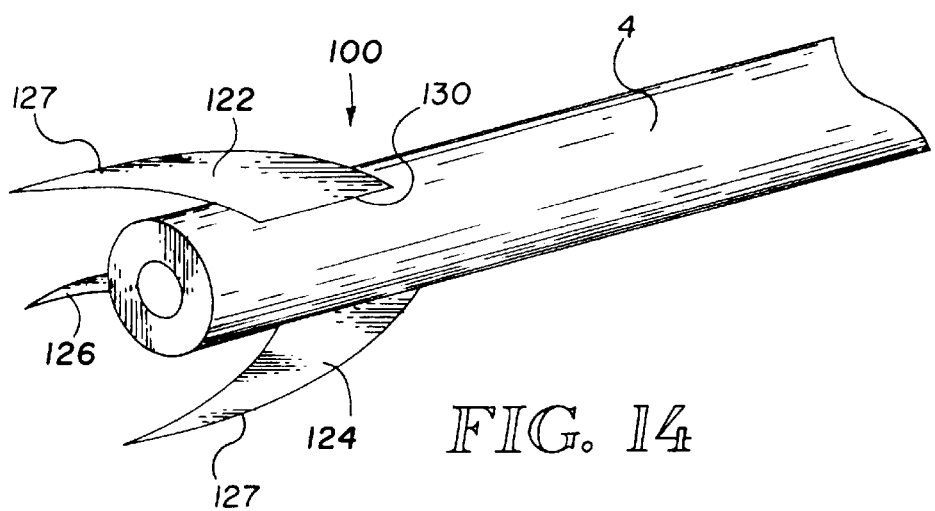
FIG. 14

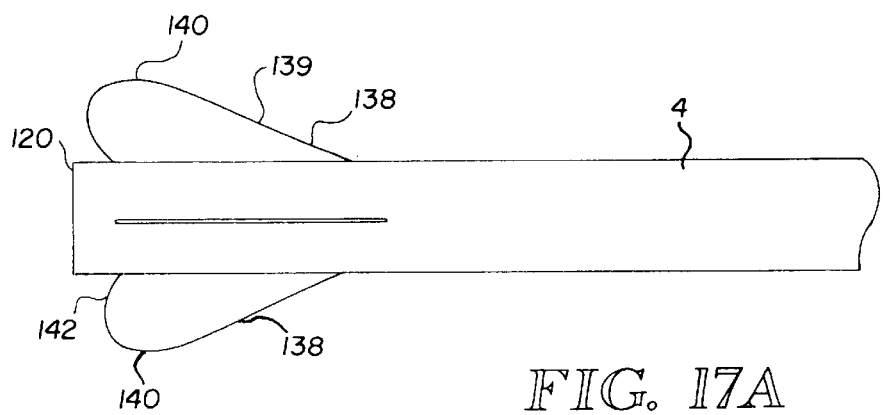
FIG. 17A
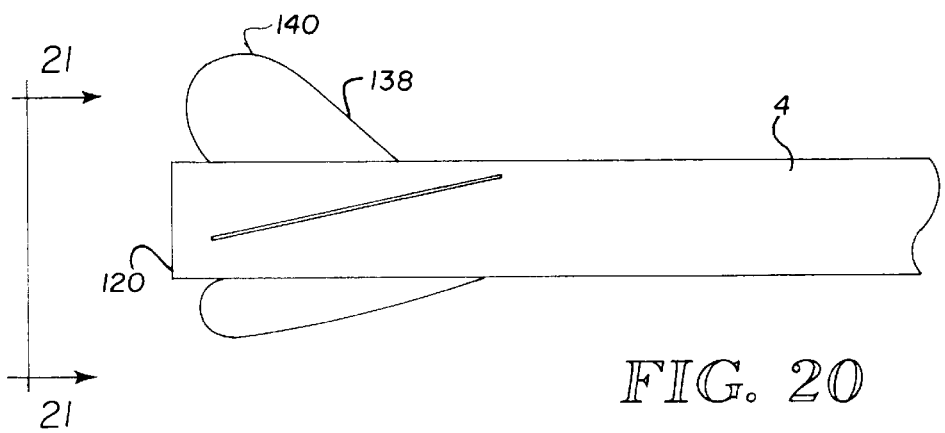
FIG. 20
FIG. 18
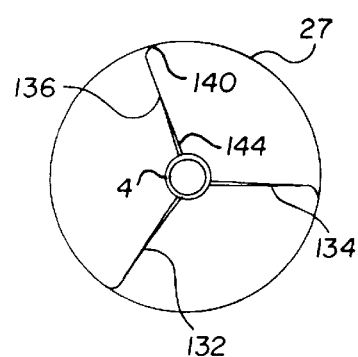
FIG. 19
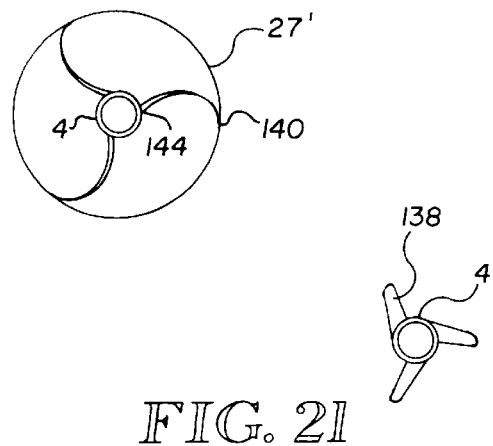
FIG. 21

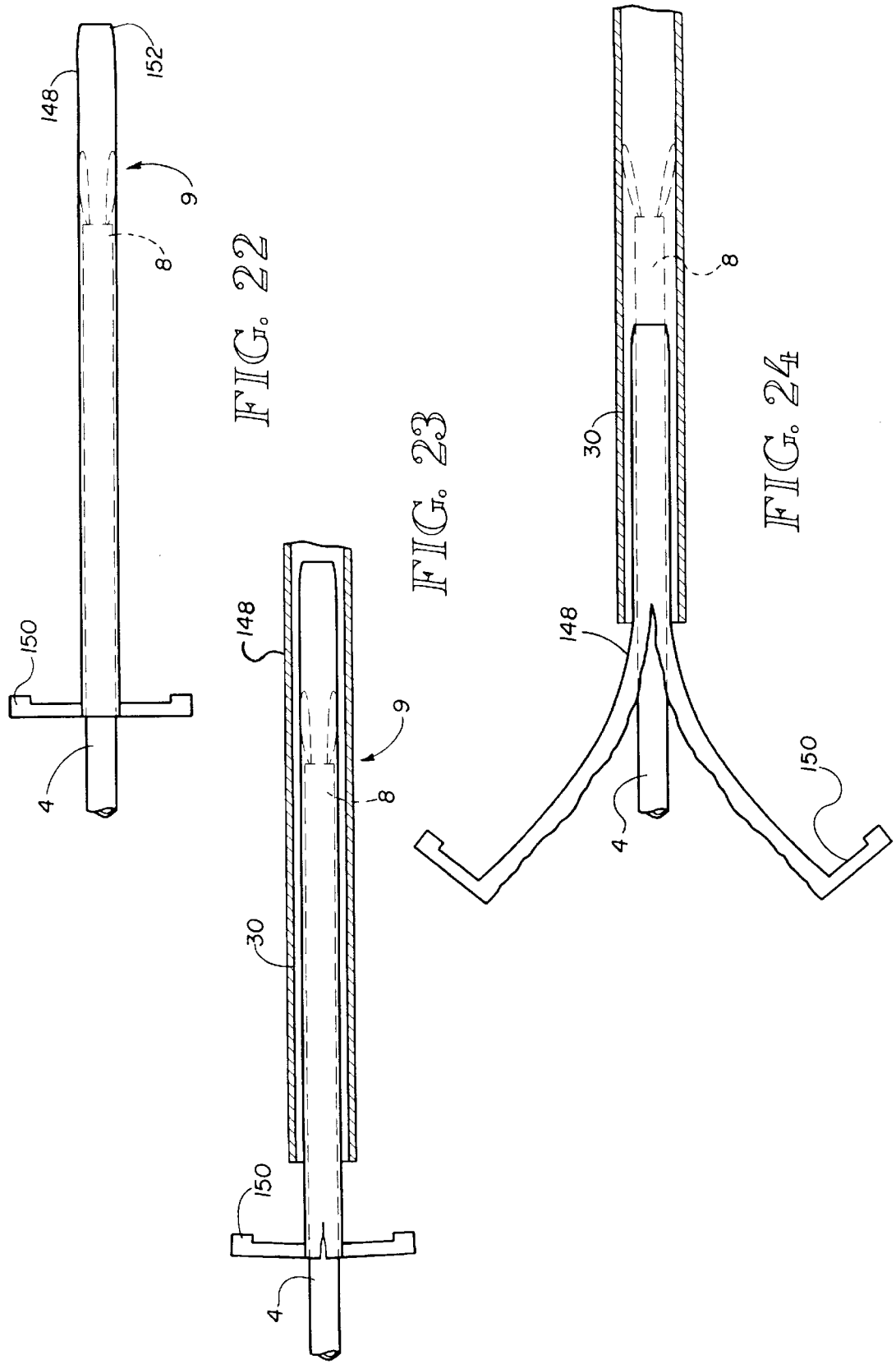

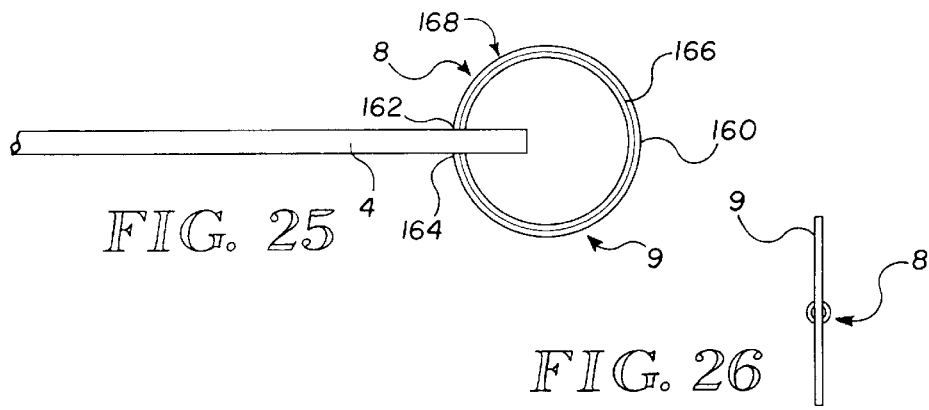
FIG. 25   FIG. 26
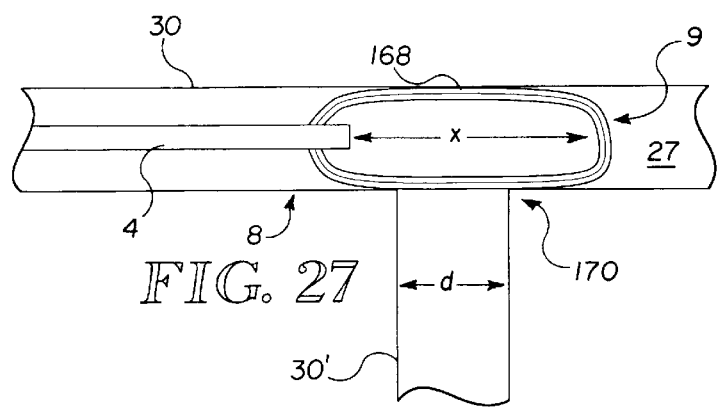
FIG. 27
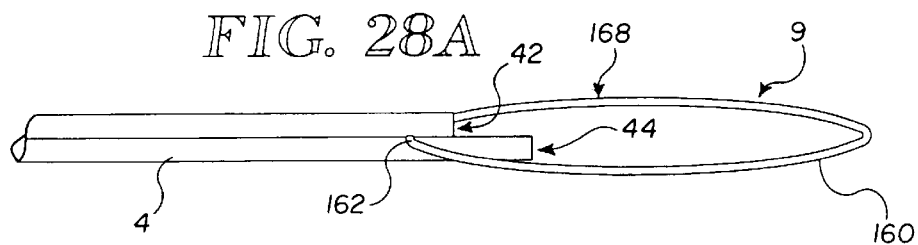
FIG. 28A
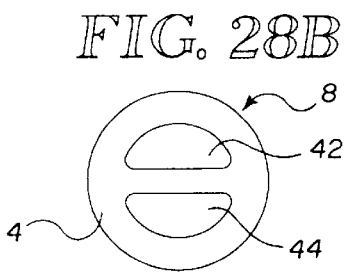 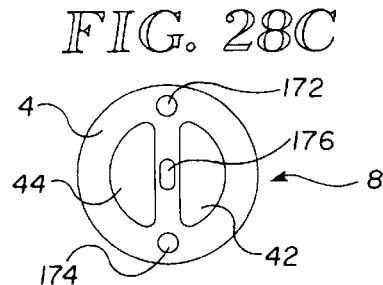
FIG. 28B   FIG. 28C

APPARATUS AND METHOD FOR RETAINING A CATHETER IN A BLOOD VESSEL IN A FIXED POSITION

CROSS-REFERENCE TO RELATED APPLICATIONS

This application is a continuation of U.S. patent application Ser. No. 08/137,619, filed Oct. 15, 1993 now U.S. Pat. No. 5,509,900 which is a continuation in part of U.S. patent application Ser. No. 07/844,715, filed Mar. 2, 1992 now abandoned.

TECHNICAL FIELD

This invention relates to intravascular catheters that have means for reducing stenosis and thrombosis at the tip of the catheter.

BACKGROUND OF THE INVENTION

The treatment of a number of medical conditions requires the placement of catheters within a patient's blood vessel for an extended period of time. These longterm applications include blood access for hemodialysis, chemotherapy, parental nutrition, blood transfusions and blood sampling.

Vascular access with catheters was first introduced more than 20 years ago. With the advent of soft, flexible silicone double lumen catheters, both acute and chronic hemodialysis became a routine procedure. Although subclavian dialysis catheters are easily inserted and well tolerated, catheter lifespan averages about three months. This is of great concern to patients on maintenance dialysis.

It is well known in the medical field that chronic placement of a catheter in a patient's blood vessel often results in catheter failure due to aspiration of the blood vessel wall into the tip of the catheter, clot or thrombus formation at the tip of the catheter, or stenosis around the tip of the catheter. A catheter failure resulting from one or more of these mechanisms is evidenced by an inability to aspirate and/or infuse fluid through the catheter, generally referred to as catheter occlusion. Typically, catheter occlusions caused by aspiration of the blood vessel wall or clot formation at the catheter tip may be resolved by repositioning the catheter tip or infusing antithrombotic agents.

Stenosis is a narrowing of the blood vessel lumen as seen in a venogram and, in general, can be due to either the formation of a thrombus within the blood vessel or a thickening of the blood vessel wall. The generally accepted view is that stenosis around the tip of a catheter implanted within a blood vessel is due to the formation of a thrombus resulting from a biochemical reaction to the introduction of a foreign material into the blood vessel. Previous attempts to prevent catheter occlusion have centered around thrombo-resistant coatings on the catheter surface in order to prevent the biochemical reaction of the patient's blood to the material of which the catheter is formed.

Prior art related to the present invention deals with the placement of stents within a diseased blood vessel to treat the problems associated with stenosis. Stents range from simple wire meshes used in U.S. Pat. No. 4,800,882, to a canister made of hydrophilic plastic which expands upon placement in a blood vessel as in U.S. Pat. No. 4,434,797. Stents are typically secured to a deployment catheter for insertion into the patient's blood vessel via a percutaneous procedure. Surgical placement of these stents is achieved by feeding the catheter from a distant site, e.g., a percutaneous puncture into the femoral artery, to the stenosis target. The deployment catheter is then removed, leaving the stent within the blood vessel lumen.

Prior publications on the subject of mounting devices in the blood stream include "Registration of Phoric Changes of Blood Flow by Means of a Catheter-Type Flowmeter," by Heinz Pieper printed in The Review of Scientific Instrument 29(11):965–967, November 1958, and U.S. Pat. Nos. 4,425,908; 4,936,823; 4,813,930; 5,135,517; and 4,654,028. However, none of these address and solve the problems presented in the field of the present invention.

SUMMARY OF THE INVENTION

The present invention is directed to an intravascular catheter that has means to retain the tip of the catheter within a blood vessel lumen such that the tip of the catheter is prevented from contacting the wall of the blood vessel. This prevents repeated impact between the catheter tip and blood vessel wall. This reduces denudation and damage to the endothelial and smooth muscle cells that line the blood vessel wall. By reducing damage to these cells, the invention allows for the cells to continue to release the bioactive molecules that normally prevent and reverse the thrombotic and coagulation processes in blood.

Most vascular injury research is in the area of arterial injury; however, the mechanism that regulates cellular growth in injured veins is not known. It is a reasonable assumption that the "response to injury hypotheses" proposed in Ross, R., Glomset, J. A., "The Pathogenesis of Atherosclerosis," N. Engl. J. Med. 2:369–77, 1976, can also be applied to injuries in the venous system. This hypothesis is based on the following observations after injury to the lumen of the blood vessel: (1) platelet adherence and degranulation precedes smooth muscle cell proliferation; (2) intimal thickening in injured arteries of thrombocytopenic animals is reduced; (3) platelet granules contain potent mitogens for cultured smooth muscle cells. Based upon these observations, Ross and Glomset suggested that a high local concentration of growth factors, particularly platelet-derived growth factors released from degranulating platelets could stimulate smooth muscle cell proliferation. Their hypothesis is based on a relationship between the thrombosis that occurs within an injured vessel and the subsequent cell growth associated with repair of the injured vessel wall.

Normally, hemostasis results from a delicate balance between clot-stimulating and clot-inhibiting processes. Endothelial cells and smooth muscle cells in a normal blood vessel are probably the main source of clot regulating factors such as heparin or heparan sulfate. These heparin and heparin-like molecules prevent the adherence of blood proteins and platelets to the surface of a normal blood vessel. Since the endothelium is a critical component of hemostasis control, localized injury and denudation of the endothelium by repeated impact with a catheter tip results in a shift of this delicate balance toward clot and thrombus formation within a denuded region. This clot formation may occur even if the catheter is composed of a material that normally would not create a reaction in the body.

Physical damage to the wall of the blood vessel affects the release and production of a number of growth-stimulating factors such as basic fibroblast growth factor and platelet-derived growth factor. These growth factors help to overcome the antiproliferative activities of the heparan sulfates, thus helping to initiate cellular proliferation and the migration of smooth muscle cells that ultimately leads to stenosis. Therefore, preventing physical damage to the endothelial cell lining of the blood vessel wall reduced stenosis, as well as thrombosis, at the tip of the catheter.

Prior art catheters allow chronic and repeated contact between the catheter tip and the wall of the blood vessel, resulting in damage to the blood vessel as discussed previously. The tip of the catheter may repeatedly bump into different locations inside the blood vessel, or the same location a number of different times, causing a reaction, or worse, damage to the vessel wall. Further damage is caused by the aspiration of the blood vessel wall into the catheter lumen. This occurs when blood is withdrawn through the catheter, such as in the performance of dialysis.

The present invention solves the problems by approaching them from an entirely different view than the prior art attempts; namely, by preventing repeated impact between the catheter tip and the blood vessel wall. The inventor has found that repeated impact with the vessel wall and a catheter tip, even if it is a soft tip, causes a physical reaction in the blood vessel wall. This reaction occurs because of repeated contact between the catheter tip and the wall of the blood vessel even if the catheter tip is soft, and even if the tip is properly coated with antithrombotic agents. This catheter-induced reaction in the blood vessel wall may lead to the formation of a mural thrombus and/or abnormal cellular proliferation within the blood vessel wall, thus resulting in stenosis and catheter occlusion. Prior art efforts to prevent catheter occlusion through the use of thrombo-resistant coatings do not alleviate the physical reaction that the catheter tip may cause to the blood vessel wall by repeated impact. Therefore, chronic placement of a catheter in a patient still results in catheter occlusion in the majority of cases.

In accordance with aspects of the present invention, chronic contact between and aspiration of the blood vessel wall by the catheter tip is prevented. This reduces damage to the endothelial cells lining the blood vessel, thus reducing catheter occlusion due to stenosis and thrombosis. In addition, the occurrence of catheter occlusion resulting from aspiration of the vessel wall will be reduced.

The present invention includes, in one embodiment, an antistenotic intravascular catheter for insertion into a blood vessel. The catheter includes a tip retainer, located at the distal end of the catheter, for retaining the tip of the catheter within the blood vessel and preventing the catheter from contacting the wall of the blood vessel. The tip retainer positions the tip of the catheter within the blood vessel without substantially obstructing fluid flow through the blood vessel. The catheter also includes an internal passageway for permitting fluids to pass through the catheter. Preferably, the catheter is a double lumen catheter of the type used generally in kidney dialysis.

In all embodiments, the tip of the catheter is retained in the blood vessel by anchoring the tip with respect to the wall of the blood vessel. Advantageously, the tip retainer permits some movement of the catheter tip with respect to the vessel wall, such as slight movement forward and back or side to side with the pulsation of the blood flow. However, movement is restricted to minimize repeated contact (or all contact) of the tip with the blood vessel wall. Just as the anchor of a ship anchors a ship to the bottom but permits some movement of the ship as the water rises and falls or flows, similarly the tip retainer can be said to anchor the tip to the vessel wall but still permit some movement of the tip based on changes of the flow in which it is anchored.

Numerous alternative embodiments are disclosed for the tip retainer. In some embodiments, the tip retainer does not penetrate the wall of the blood vessel. In one embodiment, the tip retainer includes a penetrating member that does penetrate the blood vessel wall. In all embodiments, the tip of the catheter is retained in the blood vessel by anchoring the tip with respect to the wall of the blood vessel.

In one preferred embodiment, the tip retainer is two or more loops of wire that flex outward and contact the wall. The loops do not penetrate the wall tissue, but do anchor the tip in a fixed position in the blood vessel, retaining it in the blood flow and preventing contact of the tip with the vessel walls.

In another preferred embodiment, a single loop extends from the tip portion of a double lumen catheter. The single loop is composed of a flexible wire coated with silicone, silicone tubing or, alternatively, is composed of silicone tubing alone. The diameter of the loop is selected to be sufficiently large that the loop bridges any branches in the blood vessel which are likely to be encountered when the catheter is positioned within the blood vessel.

As a further alternative, the silicone tubing which forms the loop may be in fluid communication with the lumen of the catheter separate from the lumen used for the kidney dialysis. Medication can be delivered through the lumen for delivery to the walls of the blood vessel at the point of contact by the loop. This provides the distinct advantage that anticoagulant medication can be delivered specifically to walls of the blood vessel near the catheter tip.

In a further embodiment the tip retainer includes fletching to anchor the catheter tip in the blood vessel. Alternatively, the tip retainer is a plurality of single straight wires that are prestressed to flex outward or straight wires with loops on the end.

In accordance with one embodiment of the invention, the tip retainer includes penetration means for penetrating the wall of the blood vessel and preventing the tip of the catheter from moving longitudinally within the blood vessel. In this embodiment, the tip includes a loop for limiting the depth of penetration.

In one embodiment of the invention, a plurality of members run from the proximal end of the catheter to the distal end where they extend radially outward until they contact the wall of the blood vessel. In this embodiment, the catheter includes withdrawal means for withdrawing the positioning means into the catheter such that the positioning means is prevented from damaging the wall of the blood vessel when the catheter is withdrawn from the blood vessel. The withdrawal means includes a guideway that runs from the proximal end of the catheter to the distal end of the catheter. The positioning means extends from the proximal end to the distal end of the catheter within the guideway.

According to one aspect of the present invention, a method for reducing catheter failure due to stenosis or thrombosis at a catheter tip is provided.

Positioning means is attached to the catheter tip, and the catheter tip and attached positioning means are placed within the blood vessel without substantially obstructing fluid flow through the blood vessel and such that the catheter tip is prevented from contacting the blood vessel wall.

BRIEF DESCRIPTION OF THE DRAWINGS

FIG. 3 is an enlarged perspective view of the distal end of a second embodiment of the tip retainer.

FIG. 4 is an enlarged perspective view of an alternative embodiment for connecting the tip retainer to the catheter.

FIG. 12 is an enlarged view of a further alternative embodiment of the tip retainer.

FIG. 13 is an enlarged view of a further alternative embodiment of the tip retainer.

FIG. 14 is an enlarged view of a further alternative embodiment of the tip retainer.

FIG. 17A is a top view of the embodiment of FIG. 15 using fletching attached straight as the tip retainer.

FIG. 18 is an end view of the embodiment of FIG. 17A as installed within a large blood vessel.

FIG. 19 is an end view of the embodiment of FIG. 17A as installed in a small blood vessel.

FIG. 20 is a top view of an alternative embodiment using fletching attached at a cant as the tip retainer.

FIG. 21 is an end view of the embodiment of FIG. 20.

FIGS. 22–24 illustrate a further alternative embodiment for placing the catheter having the tip retainer on the end thereof within a blood vessel.

FIG. 25 is a side elevational view of a further alternative embodiment of the tip retainer.

FIG. 26 is an end view of the embodiment of FIG. 25.

FIG. 27 is a side elevational view of the catheter having the tip retainer of FIG. 25 in one of the possible positions inside a blood vessel.

FIG. 28A is an enlarged view of a further alternative embodiment of the retainer and catheter.

FIG. 28B is an end view of the catheter used in the embodiment of FIG. 28A, without the tip retainer shown.

FIG. 28C is an end view of a further alternative embodiment of the catheter of FIG. 28A without the tip retainer shown.

FIG. 39B is a side elevational view of the embodiment of FIG. 38A with the tip retainer in a bode position for positioning within a blood vessel.

DETAILED DESCRIPTION OF THE INVENTION

Figure 1:
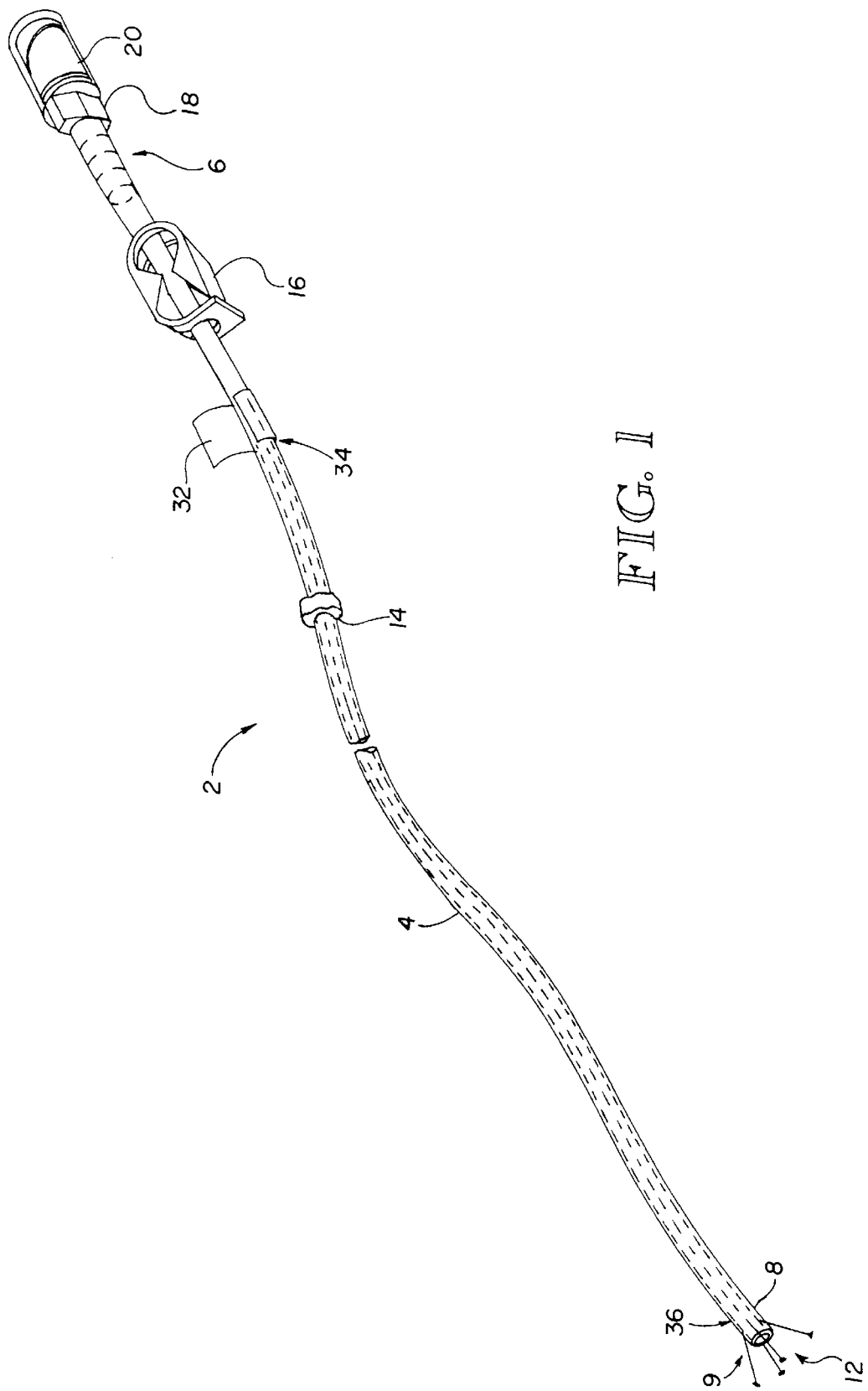
FIG. 1 is a perspective view of a first preferred embodiment of the antistenotic intravascular catheter of this invention.

FIG. 1 is a perspective view of a first preferred embodiment of an antistenotic intravascular catheter 2 of the present invention. Catheter 2 includes a tube 4 formed from a material suitable for placement in a blood vessel, such as silicone rubber. The catheter includes a Dacron anchor cuff 14 for anchoring the catheter subcutaneously. An in-line clamp 16, for preventing fluid flow, is placed on tube 4 adjacent the proximal end 6. The proximal end 6 of the catheter is attached to a luer-lock adapter 18 which is sealed by threading an injection sealing cap 20 onto the adapter in a manner known in the art.

Figure 2B:
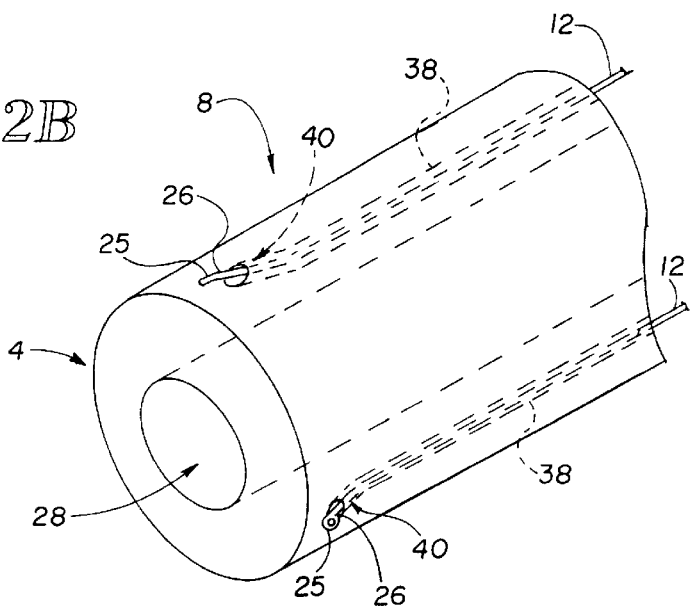
FIG. 2B is an enlarged perspective view of the preferred embodiment of FIG. 2A showing the tip retainer after it has been partially withdrawn into the guide tube.
Figure 2A:
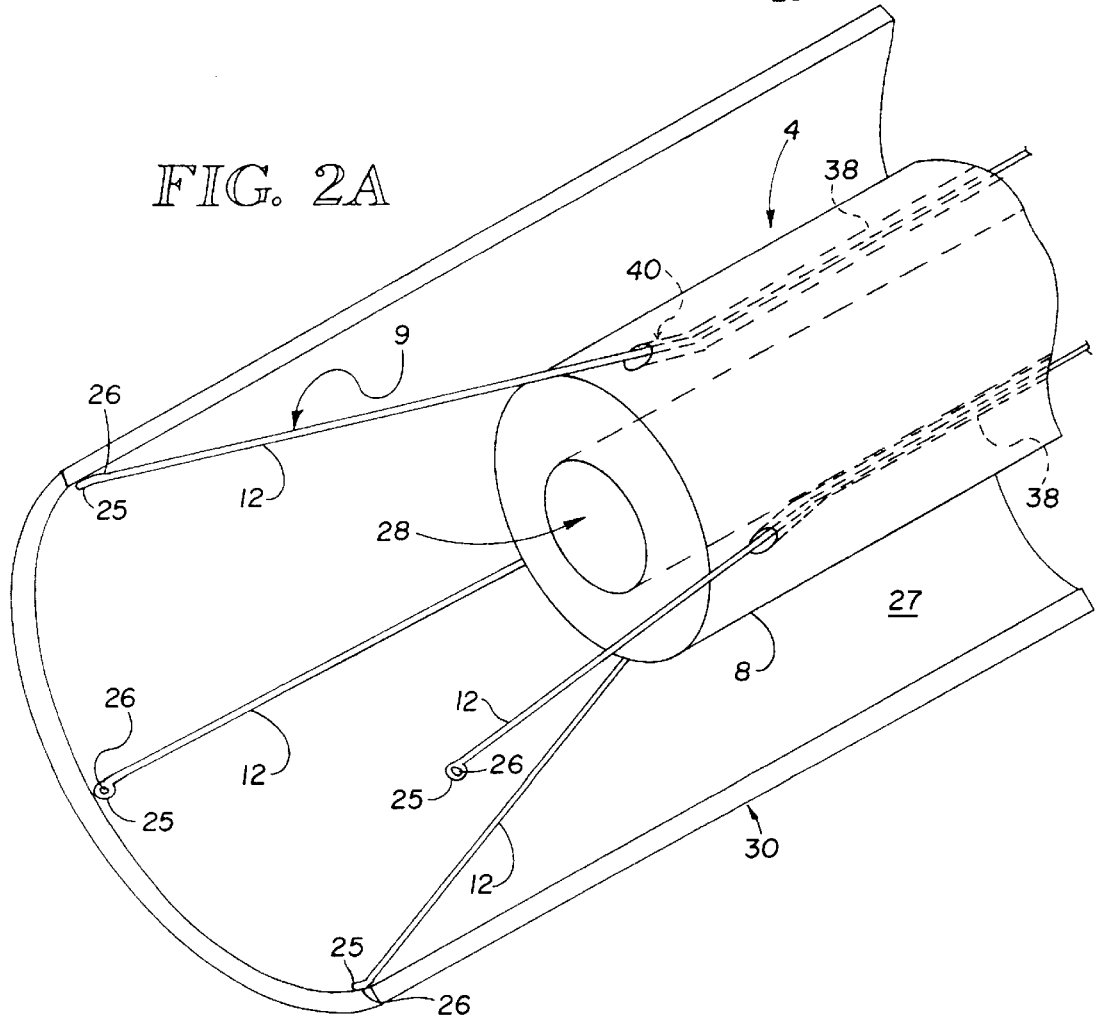
FIG. 2A is an enlarged perspective view of a first preferred embodiment of the tip retainer as deployed.

According to one aspect of one embodiment of the present invention, the intravascular catheter 2 includes a tip retainer 9 for retaining the distal end 8 in the bloodstream and preventing the tip of the catheter from contacting the wall of a blood vessel 30 as shown in FIG. 2A.

In a first embodiment, the tip retainer 9 includes four wires 12 positioned within the catheter wall and extending along the length of the catheter, from the distal end of the catheter towards the proximal end 6 of the catheter. This ensures that the proximal ends 34 of the wires 12 will be accessible outside the patient's body after the catheter has been implanted in a blood vessel 30. The proximal ends 34 of the wires 12 are secured to the catheter by an appropriate method such as heat shrink Teflon™ tubing 32 that is placed over the wires and shrunk in place. The proximal end of the wires could also be secured through the use of a band integrally formed in the tube 4 or other structures which prevent movement of the proximal end 34 of the wires 12 until they are controlled by a physician.

The wires 12 are preferably made of or coated with a material which does not cause an adverse reaction when placed in the patient's body. Suitable materials include stainless steel, titanium, some plastics such as nylon, some composite materials, and Teflon™ coated wires, including Teflon™ coated stainless steel. Depending upon the application, the wires 12 have a diameter ranging from 0.0025 to 0.076 cm. In some applications, it may be desirable to treat the wires 12 with an antithrombotic coating, for example, dipping or plating the wires in a coating or applying a coating through plasma polymerization in order to reduce blood clotting on the wires. Plasma polymerization is explained in detail in Yeh et al., "Blood compatibility of surfaces modified by plasma polymerization," *Journal of Biomedical Materials Research* 22:795–818, 1988.

As shown in FIG. 2A, in one embodiment, the wires 12 extend along the length of the catheter through guideways 38 and exit the guideways at openings 40. The guideways 38 protect the wires 12 while also maintaining proper positioning between the individual wires. Guideways 38 and wires 12 are preferably extruded as an integral part of tube 4, or alternatively are extruded individually and are later attached onto the outside of the tube 4 or inserted into tube 4. In the embodiment shown, four wires 12 are used, however, a different number of wires, such as three or five, could be used, depending upon the application.

Preferably, the four wires 12 are equally spaced circumferentially around the distal end 8 such that they serve as a tip retainer 9 and positioning means for positioning the tip of the catheter within the blood vessel 30. The tip retainer ensures that the tip of the catheter does not contact the inner wall 27 of the blood vessel 30. The thin wires 12 restrict movement of the tip of the catheter to prevent it from hitting the inner wall 27 while not substantially obstructing the fluid flow through the blood vessel and not causing clots.

In the embodiment illustrated in FIG. 2A, a loop 25 is formed near the end of each wire 12, and a short penetration prong 26 is formed that extends outwardly from each loop. The prongs 26 penetrate the wall of the blood vessel 30. Each prong 26 is sized and extends from loop 25 such that the prong penetrates the wall of the blood vessel to a depth in the range of 0.1 to 3 mm after placement within the blood vessel. The loops 25 serve as limiting means for limiting the depth to which the prongs 26 penetrate. This prevents the tip 8 of the catheter from moving longitudinally within the blood vessel 30.

Other structures could also be used to perform the penetration and depth limiting functions. As an example, instead of forming a loop near the end of each wire, an enlarged section such as thickening of the wire band welded or bonded to the wire or a bend near the tip of the wire could be used.

The distal end of the catheter is retained within the blood vessel and prevented from contacting the endothelial cells lining the blood vessel by rubbing or aspirating the wall of the blood vessel by the tip retainer 9. Additionally, noncontact damage to the endothelial cells of the blood vessel, such as through fluid dynamics wherein the force of the flow of fluid around the openings of the catheter may cause cellular damage, is believed to be reduced by the present invention. Although penetration of the wall 27 by prongs 26 causes some damage to the blood vessel, the damage caused is not significant in comparison to the damage that would be caused by repeated impact or chronic rubbing of the tip 8 or by aspiration of the inner wall 27, which may occur with prior art catheter designs. By reducing the contact with and damage to the endothelial cells, the present invention allows for the continued release of anticoagulant molecules by the endothelial cells in the vicinity of the distal end of the catheter as explained previously. Correspondingly, there is a reduction in thrombosis and/or stenosis of the blood vessel lumen at the distal end of the catheter and thus reduced catheter occlusion.

The antistenotic intravascular catheter 2 (FIG. 1) may be placed within the blood vessel 30 using a sheath introducer of the type shown in more detail in FIGS. 22–24, an embodiment of which is explained with respect to those Figures. In one embodiment, a tubular introducer sheath is inserted within a patient's blood vessel, with the sheath terminating at the point within the blood vessel where the distal end 8 of the catheter is to be placed. The catheter 2 is then placed within the introducer sheath with the wires temporarily constrained along the catheter's longitudinal axis by the sheath. The catheter is then pushed down the sheath until the distal end 8 of the catheter exits the introducer sheath. As the distal end of the catheter exits the introducer sheath, the wires 12 spread radially to contact and penetrate the blood vessel wall as shown in FIG. 2A. After placement of the catheter into the blood vessel, the introducer sheath is removed from the blood vessel.

Another technique for placing the inventive catheter tip retainer within the blood vessel wall is with an inflatable balloon. Small balloons for insertion into the blood stream and methods to inflate them are known in the field of medical treatment devices. According to one aspect of installing this invention, the wires 12 are positioned circumferentially around such a deflated balloon. The balloon is then introduced into the blood vessel by any acceptable technique. When the tip of the catheter is at the proper location, the balloon is inflated and the wires 12 contact the wall 30. In the embodiment in which prongs 26 are present on the ends of wires 12, the prongs are solidly pressed and embedded into the vessel wall 30 under the force of the balloon. The balloon is then deflated and removed. If this installation technique is used, the wires 12 do not need to be spring-biased outward; the force of the balloon will press them outward into contact with the wall 30.

The catheter 2 is removed from the blood vessel by first removing the heat shrink Teflon™ tubing 32 or other structure which secures the proximal ends 34 of the wires. Each wire 12 is then withdrawn from contact with the blood vessel wall 27 into its respective guide tube 38. FIG. 2B shows the wires in this partially withdrawn position. Each wire 12 is withdrawn until the loops 25 and prongs 26 are retracted into the soft silicon rubber that forms tube 4 and guideways 38. After withdrawing each wire 12 into its respective guide tube, the catheter is withdrawn from the blood vessel using standard catheter withdrawal procedures. The ability to withdraw the prongs 26 and loops 25 into the guideways 38 reduces damage to the blood vessel upon removal of the catheter.

FIG. 3 shows the distal end of a second embodiment of the present invention. The second embodiment comprises a tube 41 with an elliptical cross section and two lumens 42 and 44 that run the length of the catheter. The second embodiment is intended to be used for hemodialysis applications in which one of the lumens is used to aspirate blood and the other lumen is used to infuse blood after dialysis. As in the first embodiment, four positioning wires 50 extend the length of the catheter within guideways 52. In the second embodiment, two of the wires 50 are located along the major axis of the elliptical tube 41 while the other wires are located along the minor axis. In this embodiment, the two wires 50 located along the major axis may extend from the tube 41 at a different angle than the two positioning wires which are located along the minor axis. Each wire 50 has a loop 54 and tip 56 near its end. The tips 56 serve as penetration means for penetrating the wall of the blood vessel, while the loops 54 serve as limiting means for limiting the depth to which the tips 56 penetrate.

FIG. 4 shows the distal end of a third embodiment of the present invention. The third embodiment has four positioning wires 60 attached to the distal end 62 through the use of securing hoops 64 and heat shrink Teflon™ tubing 66, which is placed over the hoops and shrunk into place. The combination of the securing hoops 64 and Teflon™ tubing 66 helps ensure that the hoops 64 and wires 60 are securely attached to the distal end 62 of the catheter. In an alternate embodiment, not shown, the wires 60 could be integrally formed into the catheter, thus eliminating the need for securing hoops 64 and tubing 66.

The positioning wires 60 extend radially outward from the securing hoops 64. The wires 60 may be attached to securing hoops 64 by welding, brazing or other appropriate means. In some applications, it may be desirable to treat the wires 60 with an antithrombotic coating to reduce blood clotting on the wires, as explained for the first embodiment. Each wire 60 has a loop 68 formed near the end of the wire, such that a short penetration tip 70 extends outwardly from each loop. The prongs 70 serve as penetration means for penetrating the wall of the blood vessel, while the loops 68 serve as limiting means for limiting the depth of penetration.

This third embodiment of the antistenotic intravascular catheter is inserted into a patient's blood vessel using the same process as described for the first embodiment. Although the third embodiment is structurally simpler than the first embodiment, it requires a more complex procedure in order to remove the catheter from the patient's blood vessel. The third embodiment may be removed using a procedure similar to the catheter insertion procedure described in the first embodiment. A tubular introduction sheath of the type shown in FIGS. 22–24 is placed over the catheter at the location where the catheter enters the blood vessel, and is subsequently slid down the catheter until it reaches the distal end of the catheter. The tubular introduction sheath slides over the positioning wires 60, withdrawing the loops 68 and prongs 70 from contact with the wall of the blood vessel. After withdrawing the loops and tips into the introduction sheath, the catheter is slid within the introduction sheath and withdrawn from the blood vessel. The introduction sheath could be removed during or subsequent to removal of the catheter from the patient's blood vessel.

Figure 5:
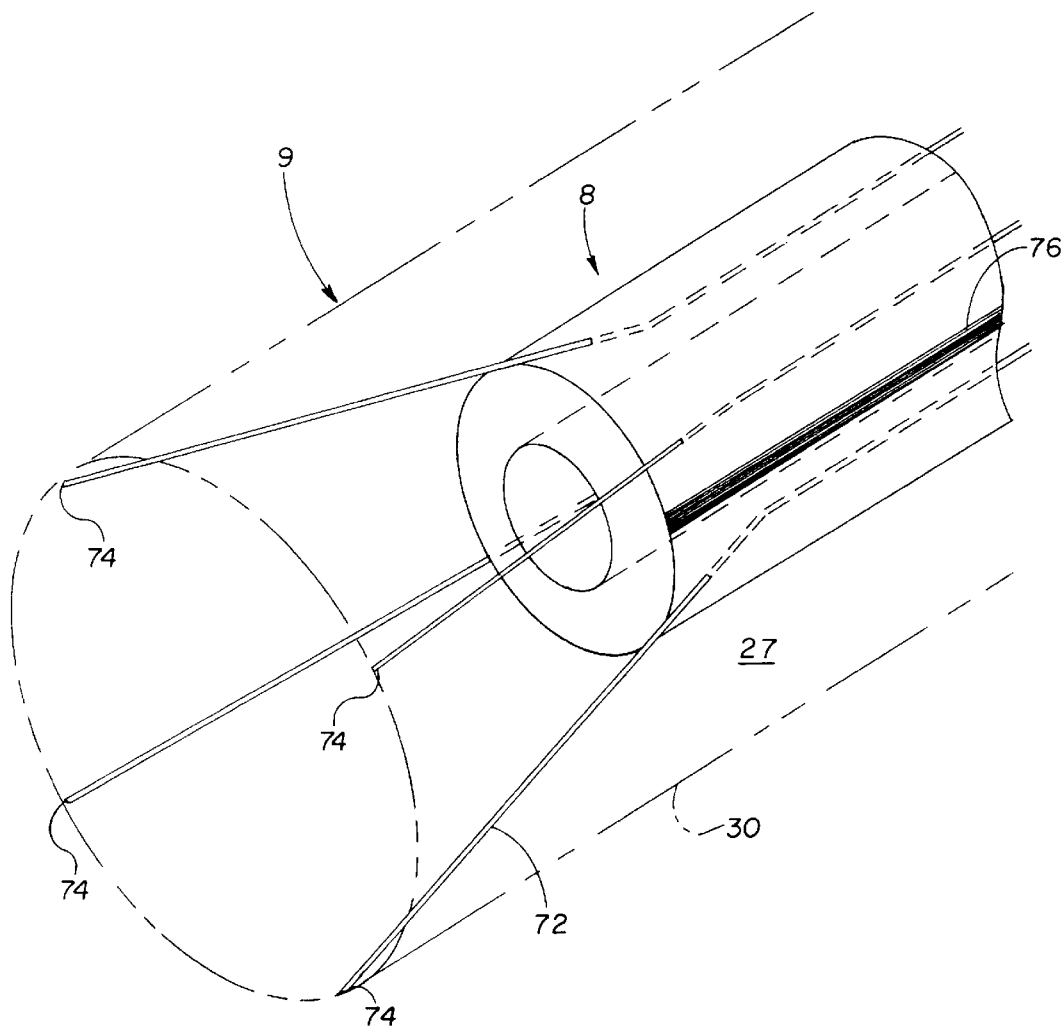
FIG. 5 is an enlarged perspective view of an alternative embodiment of the tip retainer.

FIG. 5 illustrates a tip retainer 9 at the distal end 8 of the catheter constructed according to an alternative embodiment for retaining the catheter tip within the blood flow stream and preventing the tip from contacting the inner wall 27 of the blood vessel 30. According to this alternative embodiment of FIG. 5, the tip retainer 9 includes wires 72 having a blunt terminating end 74 for contacting the inner wall 27 of the blood vessel 30. The blunt end 74 does not include a sharp tip of the type previously described with respect to tips 26, 56 and 70. Instead, the blunt end 74 contacts the inner wall 27 but does not penetrate the wall of the blood vessel 30. The four wires 72 act to anchor the tip of the catheter with respect to the blood vessel wall and retain the tip within the flow in the blood vessel while preventing the tip 8 from contacting the blood vessel wall with the advantages as previously described. The wires 72 are prestressed to be resiliently spring biased outward with an equal pressure from each of the wires 72 such that the tip 8 is generally centered within the blood vessel 30.

An indexing mark 76 is also included on the catheter tube 4, extending along the length of the catheter tube 4. The indexing mark 76 visually indicates to a user the rotational orientation of the tip 8 within the blood vessel and thus indicates the rotational orientation of the tip retainer assembly. The position of the indexing mark 76 may indicate, for example, that the rotational orientation of the tip 8 is such that one of the wires 72 is positioned where two of the blood vessels join together and is not contacting any wall of the blood vessel or providing stabilization. The user may then elect to change the rotational orientation of the tip 8 such that each of the wires 72 is firmly in contact with the blood vessel wall. This visualization could also be done, for example, with the catheter positioned within the introducer sheath.

However, one reason for providing at least three and more preferably four wires 72 is because contact with three wires is generally deemed sufficient to stabilize and retain the tip 8 such that it does not contact the wall 27. For example, the catheter 4 having the inventive tip retainer at the distal end 8 may be positioned at or near the brachial cephalic junction and there is a likelihood that one or more of the wires 12 may fall into the junction. One advantage of having multiple wires is that the tip 8 can be stably anchored even if one of the wires is not anchored to the wall because the other wires will hold it in position. Thus, even if one of the wires 72 is not contacting the blood vessel wall because it is positioned in or along the junction, the other wires 72 will be contacting the wall and will retain the tip 8 in a position to prevent it from repeatedly bumping against the inner wall 27 of the blood vessel 30.

Figure 6:
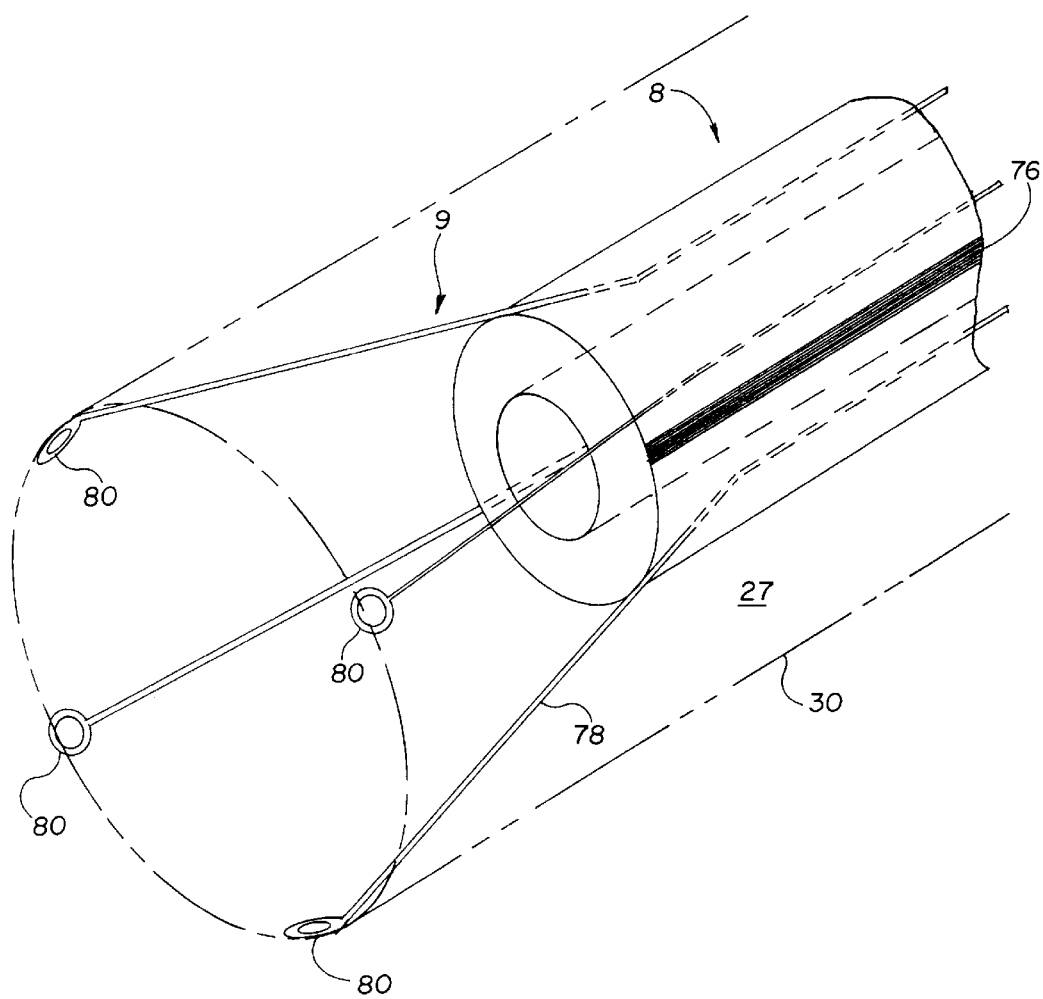
FIG. 6 is an enlarged perspective view of an alternative embodiment of the tip retainer.

FIG. 6 illustrates an alternative embodiment for the tip retainer 9 having wires 78. The wires 78 include enlarged loops 80 at their distal end. The enlarged loops 80 do not penetrate the blood vessel wall 30. Instead, they rest firmly against the inner wall 27, as an anchor to firmly retain the tip 8 in a fixed position within the blood vessel. The loops 80 have an enlarged surface area to ensure that the blood vessel wall is not penetrated while providing a firm support for the tip retainer 9. The loop 80 abuts firmly against the inner wall 27 without penetrating it in a manner similar to the anchor of a ship resting on the sea bottom but not penetrating through the sea floor. The tip retainer 9 in this way anchors the tip 8 without penetrating the wall of the blood vessel 30.

Figure 7:
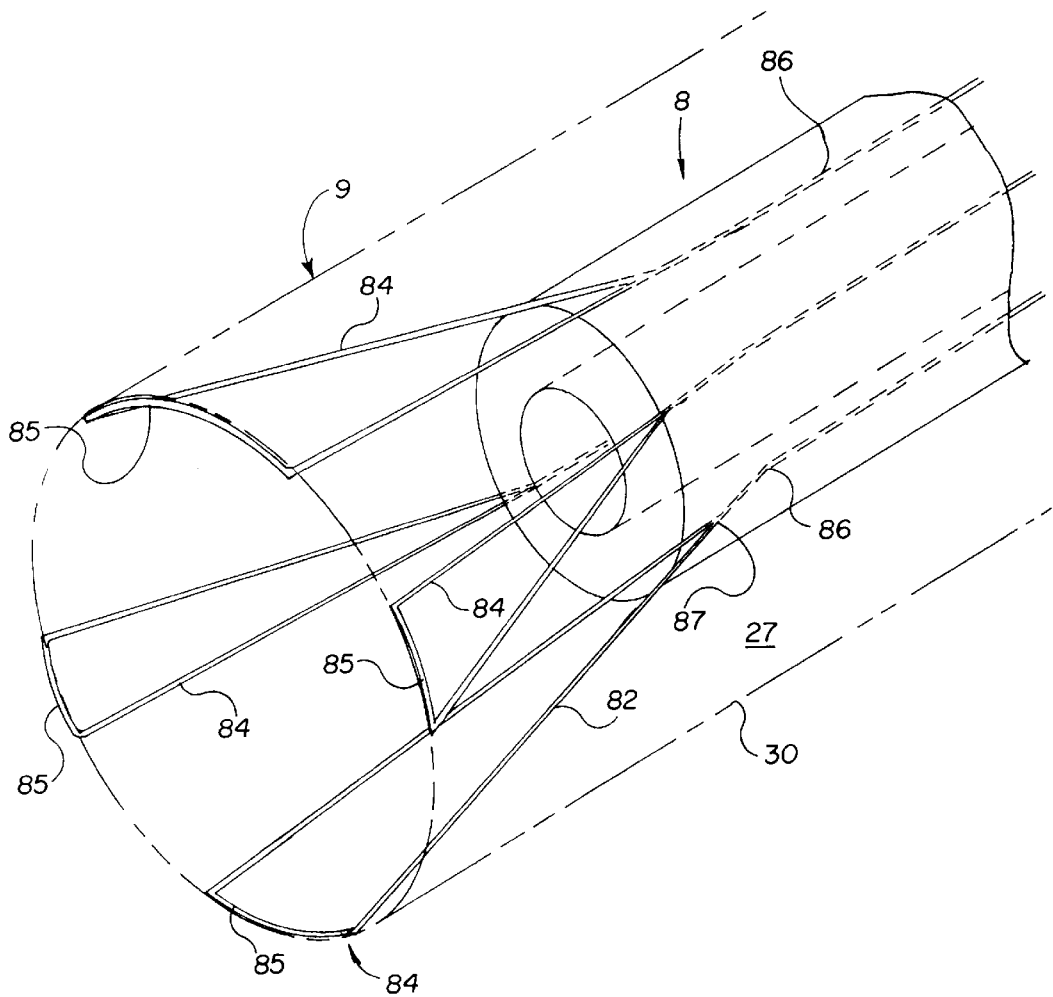
FIG. 7 is an enlarged perspective view of a further alternative embodiment of the tip retainer.

FIG. 7 illustrates an alternative embodiment of the tip retainer 9 having wires 82 formed in an enlarged loop 84. The loops 84 are formed from a single piece of wire that is bent at the end and terminates by being contacted to itself at the end 87, a single wire being within the guideway. Alternatively, the loop 84 is formed from the wire 82 being bent in half and having two sections of the wire 82 extend within the guideway 86. The two ends of the wire 82 extend out of the proximal end of the tube 4 at position 34 as shown with respect to FIG. 1. The wires 82 can therefore be extended or retracted, according to the user's preference, to provide loops 84 of a desired size and shape. The wires of the loops 84 are prestressed or bent to be resiliently spring biased outward so they extend with equal force and equal distance from the tip 8 so as to retain the tip 8 in approximately the center of the blood vessel 30. Use of loops 84 provides the advantage of broad contact area 85 with the inner wall 27 while ensuring there is no penetration of the wall. The broad contact area at a distal region of each of the loops 84 is a further aid for centering the tip 8 and ensuring that it is firmly retained within the blood flow and the blood vessel and does not contact the inner wall 27.

Figure 8:
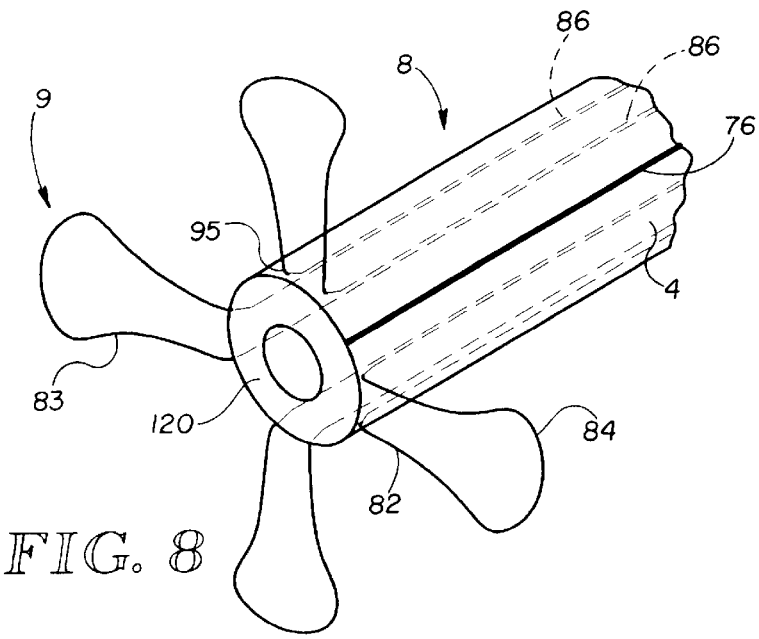
FIG. 8 is an enlarged perspective view of a further alternative embodiment of the tip retainer.

FIG. 8 is an alternative embodiment generally along the lines of FIG. 7 with the loops 84 formed in a cloverleaf arrangement. The cloverleaf shape of the wires 84 serve to further increase the contact area and provides strength in anchoring the tip 8 of the catheter 4 within the blood vessel but without penetrating the wall of the blood vessel. In one embodiment, the loops exit from the tip region 8 a selected distance 95 back from the end of the tip. Having the wires exit spaced apart from the tip end 120 decreases the risk of creating blood clots at the end 120 or forcing the lumen shut at the face 120 under a heavy spring force by the wire loops 84. The end region 8, particularly the face 120, may be constructed of a somewhat stiffer material to keep the lumen opening from being partially closed when the wire loops 84 are deployed.

In the cloverleaf arrangement of FIG. 8, each end of one wire extends down its own guideway 86, or alternatively multiple wires may extend down the same guideway 86, permitting user manipulation of individual wires. The wires may exit from the face 120 of tip 8, or, as shown, exit from a location along the sidewall and extend forward, toward the tip.

Figure 9:
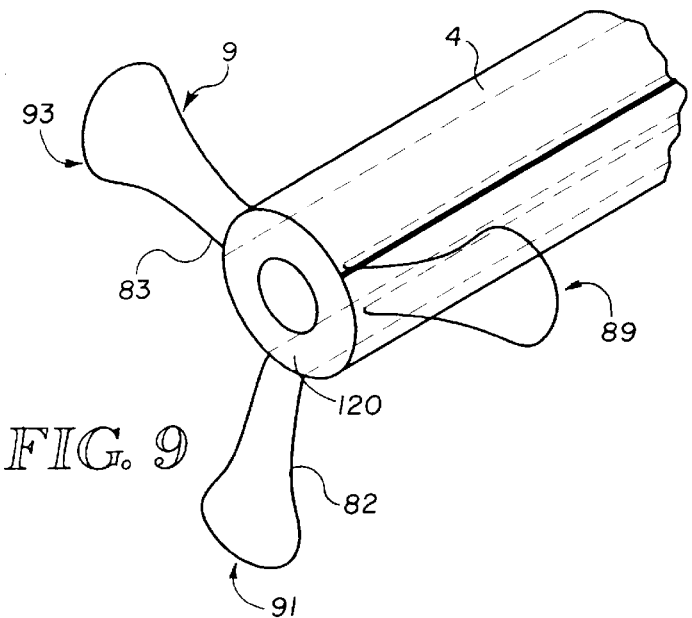
FIG. 9 is an enlarged perspective view of a further alternative embodiment of the tip retainer.

FIG. 9 illustrates an alternative embodiment for the tip retainer 9 of a three-leaf clover configuration. Three loops 89, 91, and 93 are provided that extend out of the surface of tip end 120 if desired. The three loops 89, 91, and 93 are positioned equidistant around the catheter tube 4. Using three wires provide the advantage of fewer wires in the blood flow, but still produces sufficient force for anchoring. For example, as previously discussed with respect to FIG. 5, the catheter may be installed such that the tip is at or near the brachial cephalic junction. Even if one of the loops 89 falls into the junction itself, the other two loops 91 and 93 will contact the wall and provide a stable contact to anchor the tip 8 within the vessel. The term anchor is used in this embodiment and all others herein in the broad sense of providing a general positioning of the catheter in the blood vessel. Some slight movement from side to side or back and forth is permitted by the various tip retainers as they anchor the tip 8 to the wall, just as a ship's anchor permits some ship movement but holds it generally in position.

The wires 82 of loops of FIGS. 8 and 9 are formed with a preselected resilient bias outwards as determined by their shape and construction. In some embodiments, a very light spring action is provided by having a light, resilient bias outward so that the device may be used in a wide range of size of blood vessels, from very small to very large, with assurances that the blood vessel wall will not be penetrated. In the embodiment of FIGS. 8 and 9, the spring bias force outward is easily adjusted by varying the angle of connection between the straight portion within the guideway and the loop portion 84. For example, the angle at which the straight portion 83 extends from the tip 8 can be selected at a desired angle.

One distinct advantage of the present invention over the prior art is that the catheter end 8 is retained within the flow of the blood and prevented from contacting the wall of the blood vessel without holding the catheter end 8 absolutely rigid. According to some prior art techniques, such as that described in the article of Pieper, as discussed in the background of the invention, the concept is to hold the tip as rigid as absolutely possible. While this may have some benefit in some embodiments, one distinct advantage of the present invention is that the invention will still operate properly even if the tip is permitted to move to different locations within the blood vessel. For example, the tip 8 may move to one side or the other within the blood vessel, based on movement of the patient, or of a rubbing of the blood vessel. Additionally, the tip 8 may move longitudinally, along the direction of the blood flow as the blood pulses. This is desirable in many embodiments and may actually act to relieve some of the stress created by the presence of the catheter. The tip retainer 9 includes members having a light spring force which permits some relative movement between the catheter tip 8 and the wall 27 of the blood vessel. However, the springs have sufficient force that the catheter tip rarely actually contacts the blood vessel wall, thus preventing damage to the blood vessel wall. In some of the embodiments described herein, the spring force becomes stronger as the catheter tip approaches the wall, thus serving to maintain the catheter tip in a spaced relationship from the vessel wall, even if some force is acting on the catheter tip 8 to push it toward the wall. The light spring force at an extended location of the spring permits some catheter tip movement, but as the catheter tip becomes closer to the wall, the spring force gradually increases, making it more difficult for the catheter tip to actually contact the wall. In some embodiments disclosed herein, the spring force is sufficiently strong that as the catheter gets extremely close to the wall, it is forced back with significant pressure to prevent an actual impact with the wall.

As will be appreciated, the tip retainer assembly 9 of each of the embodiments described herein may be made of or coated with an appropriate antithrombotic material that does not cause an adverse reaction when placed within a patient's body, as previously described.

The physician extends or withdraws the wires in the embodiments of FIGS. 1–9 to contact the blood vessel wall with the desired force. If the vessel wall has a large diameter, the wires are extended further. Similarly, if a high retaining force is desired, the wires can be extended slightly farther. On one hand, if the physician encounters a small vessel, or one in which a weak retaining force is sufficient to anchor the tip 8, he may withdraw the wires as necessary.

The physician also selects a catheter tip having a properly sized and spring biased tip retainer assembly 9 for his intended uses. If the spring force is found to be too weak, or alternatively, too strong, he may select another tip that is manufactured having a tip assembly 9 of a slightly different spring force, as necessary. (This may be done for each of the embodiments described herein, as desired.) Similarly, a range of loop sizes and shapes is provided to permit the physician to select the one that best suits the needs of a particular use.

The physician may observe the placement and operation of the catheter tip inside the blood vessel to ensure that it is properly anchored as the procedure progresses. This observation can be carried out with known ultrasonic imaging equipment, for example. Alternatively, the tip 8 may have a radioactive isotope or other marker placed therein to permit the physician to ensure that the tip is immobilized and not contacting the vessel wall. A fluoroscope or X-ray device may also be used to image the tip.

Often the tip must be in position in the blood vessel for an extended period. Solid placement of the tip in a position which is spaced from the wall and securely anchored with respect to the wall followed by confirmed observation of this by a physician is thus helpful to permit long-term placement of the catheter without injury to the blood vessel.

Figures 10A, 10B:
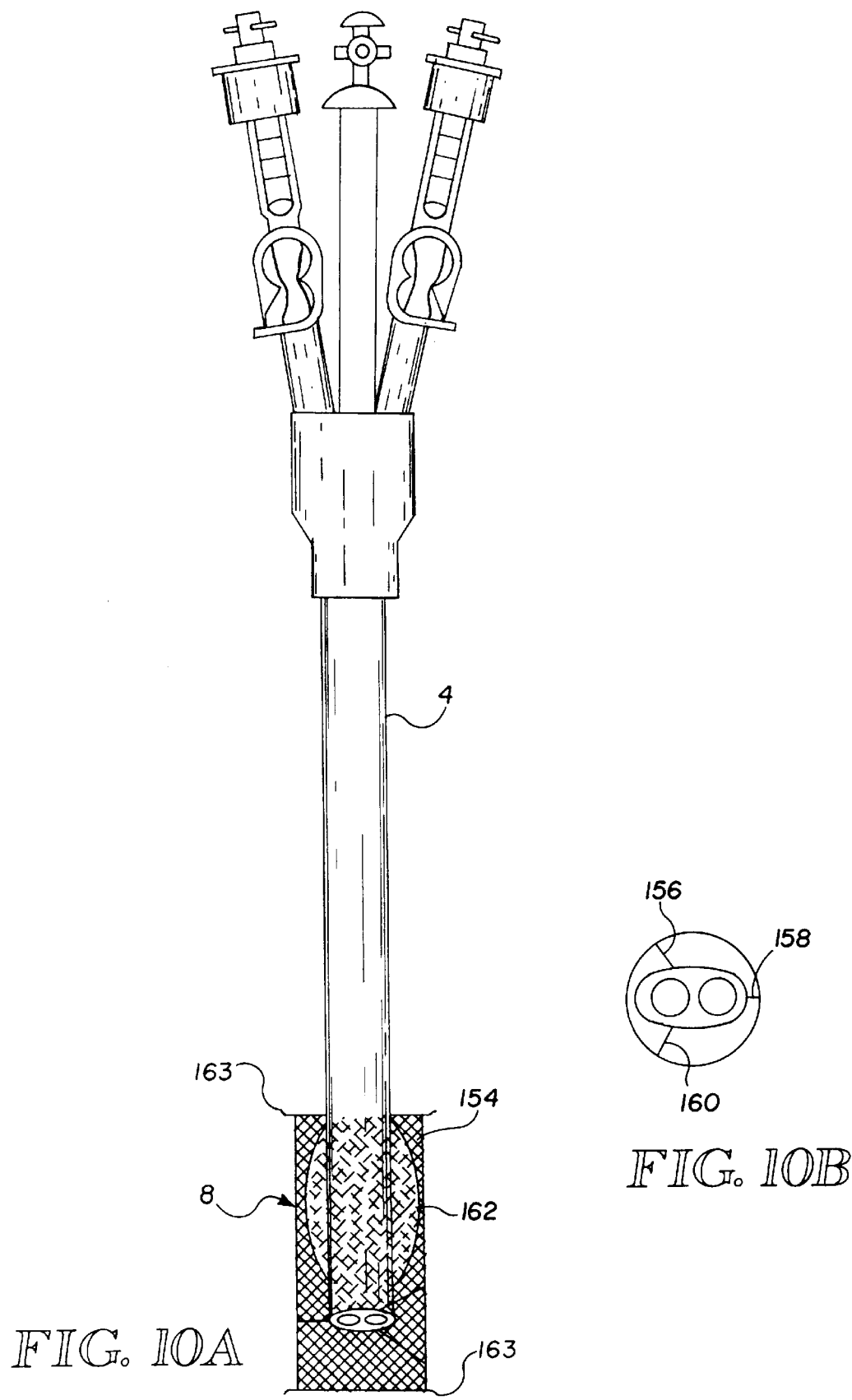
FIG. 10A is an enlarged perspective view of a further alternative embodiment of the tip retainer.
FIG. 10B is an end view of the device of FIG. 10A.

FIGS. 10A and 10B illustrate a further alternative embodiment of the invention. According to this alternative embodiment, an intravascular stent 154 is provided at the distal tip 8 of the catheter 4 for the prevention of stenosis and subsequent catheter occlusion. The stent 154 is an intraluminal vascular prosthesis constructed of braided stainless steel, or other materials. They are, of course, coated with the appropriate materials to prevent interaction with the blood.

Current applications of a standard stent include placement in the urinary system, and more recently, within arteries for arterial and coronary disease as an intraarterial wall support usually following balloon angioplasty.

To deploy the stent according to the invention, an expandable balloon 162 is positioned near the tip region 8 along the outer wall of the catheter 4, or alternatively, a rolling membrane is provided around the stent 154 and constructed near the catheter tip. The balloon 162 is covered with the self-anchoring stent 154, the entire assembly being attached along the sidewall of the catheter tube 4 when it is inserted into the blood vessel. After the catheter 4 has been inserted into the blood vessel with a tip 8 at the desired location, the balloon 162 is inflated to deploy the stent 154. The stent 154 includes prongs 163 that penetrate the wall of the blood vessel to solidly affix the stent 154 and the catheter end 8 to the wall of the blood vessel. The balloon 162 is then deflated. The stent 154 is connected to the catheter tip 8 by one or more anchoring wires 156, 158, and 160. If desired, to facilitate catheter removal, the prongs 163 may be connected to the stent 154 with prestressed breakaway points so that they may be easily broken off and the stent 154 removed. The prongs 163 may be composed of a material which is absorbed by the body over time. Alternatively, the wires 156, 158, and 160 which connect the tip 8 to the stent 154 may have prestressed breakaway points at the surface of the stent, interfacing between the catheter and the stent 154. The catheter 4 may be removed by withdrawing it, applying pressure to sever the prestressed breakaway points near the surface of the stent 154. In this embodiment, the stent 154 remains within the body and, is preferably constructed of a material which can be absorbed by the body over time rather than being constructed of stainless steel. Materials which can be absorbed by the body are well known in the art and any of those which is commonly known is acceptable for use to construct stent 154 or prongs 163.

According to the embodiment of FIGS. 10A and 10B, the stent 154 is preferably a braided mesh, or an alternative embodiment, includes a slit extending longitudinally along its entire length. Having a slit in the stent 154, or alternatively constructing it of a braided material permits the stent to be completely collapsed, in a tight position around the catheter 4 and then expanded by balloon 162 to have enlarged diameter along the inside surface of the blood vessel.

By using the techniques according to the concept of this invention, as disclosed in FIGS. 10A and 10B, as well as all other figures of this invention, the catheter tip 8 is anchored, preventing damage to the blood vessel wall and thus preventing cellular proliferation and stenosis.

Figure 11:
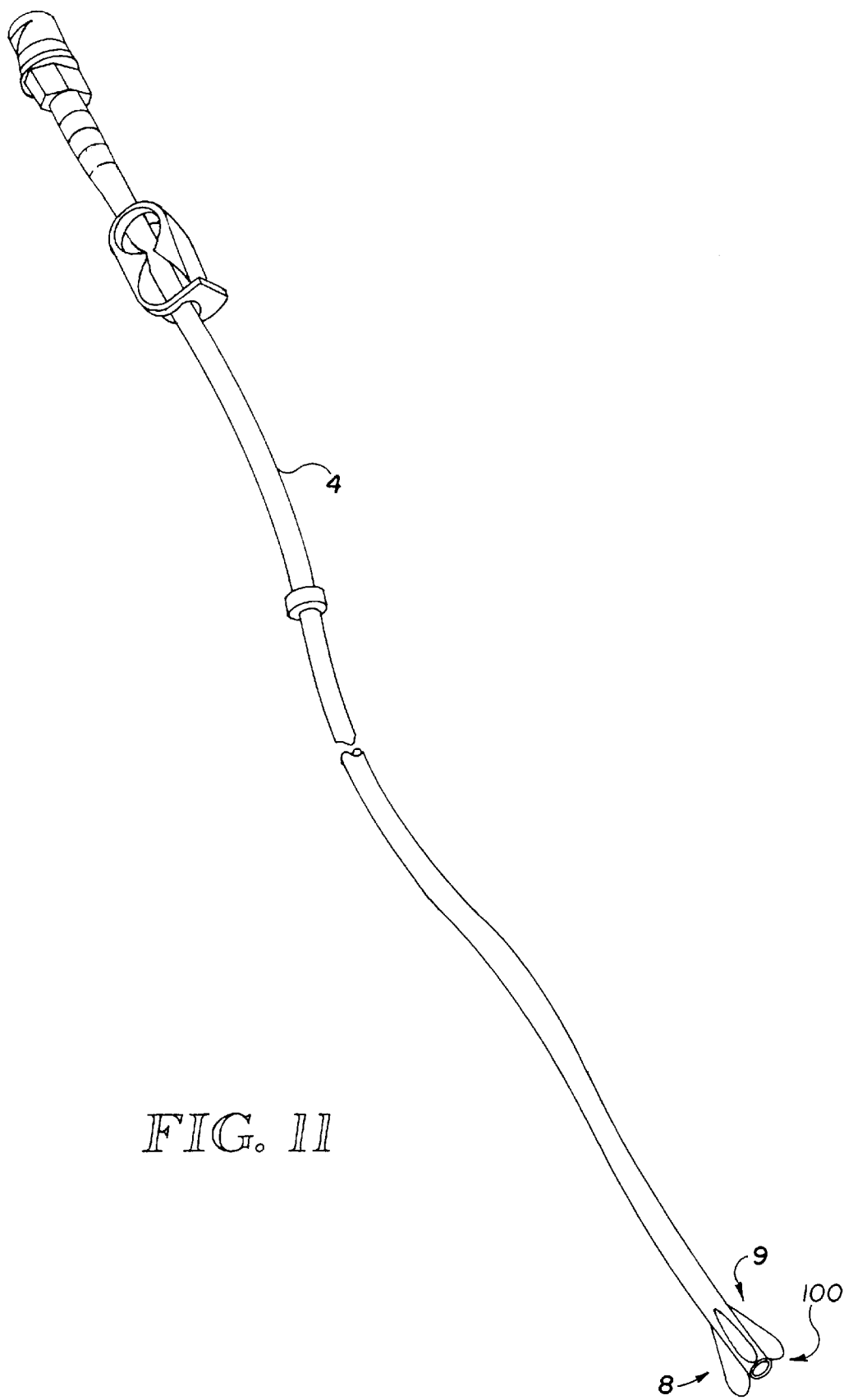
FIG. 11 is a perspective view of a further alternative embodiment of the catheter showing an alternative embodiment of the tip retainer.
Figure 15:
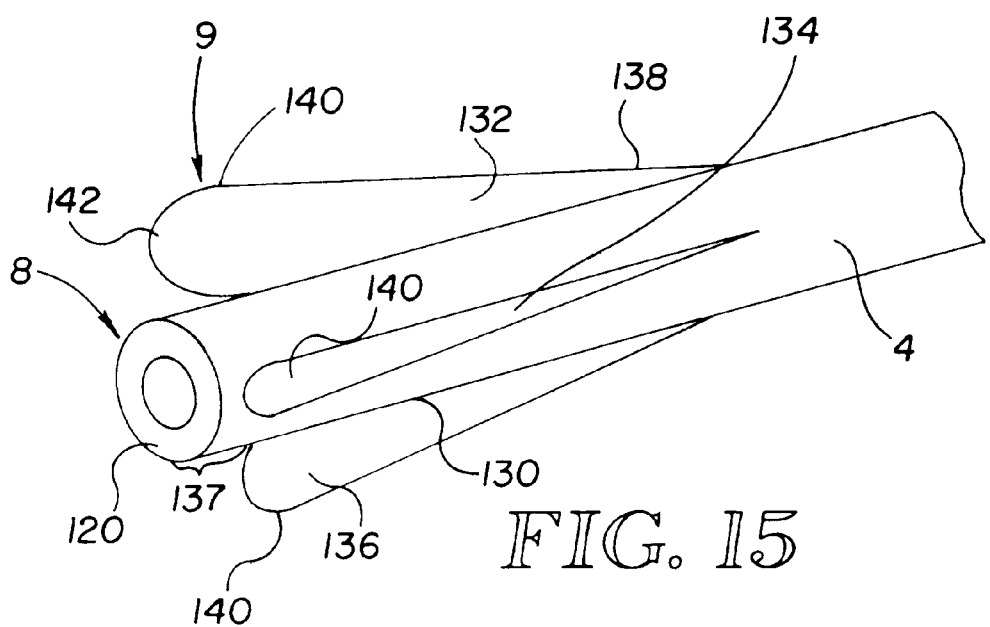
FIG. 15 is an enlarged view of a further alternative embodiment of the tip retainer.
Figure 16:
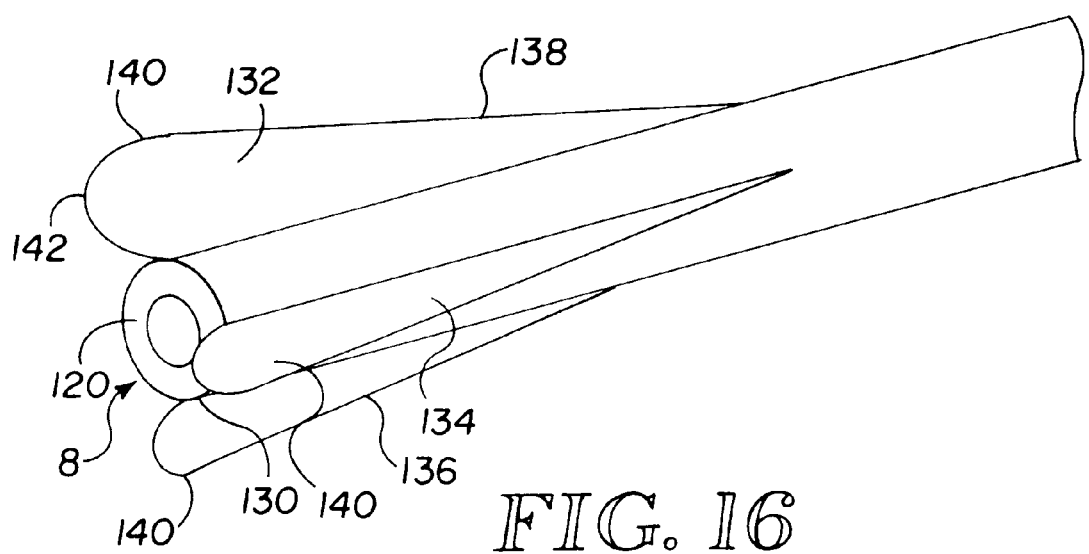
FIG. 16 is an enlarged view of a further alternative embodiment of the tip retainer.

FIG. 11 illustrates a further alternative embodiment of the catheter having a tip retainer 9 at a distal end thereof composed of fletching 100. The fletching 100 is positioned adjacent to the tip 8 or, in one embodiment, recessed back from the tip portion 8 a slight distance as shown in FIGS. 15 and 16 and explained in more detail herein.

An advantage of the use of fletching 100 is that the tip retainer 9 is constructed in which the fletching 100 is a plastic or polymer which is injection molded. In one preferred embodiment, the fletching 100 is injection molded or extruded simultaneously with the injection molding or extruding on the tube 4 so that the manufacturing cost is minimized and the entire assembly is provided as a single, unitary member.

FIGS. 12–14 illustrate alternative embodiments for the shape of the fletching 100 which provides the tip retainer assembly 9. According to the embodiment of FIG. 12, three fletchings are provided, 102, 104 and 106. The fletching 100 is composed of the same material as the tube 4, being constructed from a unitary member in a preferred embodiment. In the embodiment of FIG. 12, the fletching 102 contains a flat surface region 108. The flat surface region 108 extends circumferentially along the same radius of the catheter 4. That is, the flat surface 108 faces upward, presenting a planar surface generally at a tangent to the circular catheter 4. The fletching 102 then extends upward, away from the tip portion 8, narrowing to terminate in a tip region 110. The fletching 102 has a preselected resilient spring bias outward as it extends upward from a base region 112 towards the tip region 110. The tip region 110 contacts the wall of the blood vessel but does not penetrate the wall. The contact at the tip 110 performs the function of anchoring the tip 8 with respect to the blood vessel wall so that the tip 8 is retained in a fixed position with respect to the blood vessel wall, without contacting the wall and remaining within the blood flow. In a preferred embodiment, three fletchings are provided, 102, 104 and 106, each constructed similarly to that which has been described in detail with respect to fletching 102 and each providing a similar spring biased force outward to center the tip portion 8 within the blood vessel.

According to the embodiment as shown in FIG. 12, the tip portion 110 of each of the fletchings 102, 104 and 106 is positioned beyond the end of the tip region 8, so that the anchoring position is beyond the distal end of the tip portion 8. Providing fletchings 102, 104 and 106 that extend beyond the tip 8 is easily provided during the manufacturing process during the molding or extruding of the tubing 4, or alternatively by cutting the tip short after the extruding process so that the tip 110 extends beyond the end of the tip 8.

In an alternative embodiment the fletchings 100 are positioned such that the tip portion 110 of the fletching 102 that contacts the blood vessel wall is approximately at the end of the tip portion 8 as explained with respect to other alternative embodiments herein.

FIG. 13 shows an embodiment in which a fletching 114 has a flat planar portion 116 in generally the same orientation as the planar portion 108 of fletching 102. That is, the fletching extends flat with respect to the tubing 4, generally in the same circumferentially extending radius as the tubing 4. However, the fletching 114 has a rounded tip portion 118 providing a broader contact surface for anchoring the tip region 8 with respect to the blood vessel wall. The broad surface area 118 provides a large contact surface area to ensure that the tip portion 8 is firmly retained in the desired position, spaced from the wall a selected distance at all times. Three fletchings are provided similar to fletching 114, spaced equidistant around the tubing 4.

FIG. 13 also illustrates an embodiment in which the contacting portion 118 terminates prior to the end 120 of the tip portion 8 of the catheter tubing 4. In some embodiments, having the contact location to the blood vessel wall approximately aligned with or slightly behind the actual tip 120 of the tip portion 8 provides advantages in the operation and structure of the device.

FIG. 14 illustrates an alternative embodiment for fletchings 100 illustrating individual fletchings 122, 124 and 126. According to the embodiment of FIG. 14, the fletching 122 extends perpendicular to the catheter tubing 4. That is, the fletching 122 is vertical with respect to the catheter tube 4, like feathers on an arrow. As best shown in FIG. 14, in this embodiment the fletching is formed in a shape which curves quickly upward, and extends in a generally straight, long tapered edge 127 for an extended distance. The thin edge 127 contacts the inter wall 27 of the blood vessel, to anchor the tip portion 8 at a selected position with respect to the blood vessel wall. The fletching has an extended contact edge along the blood vessel wall, to more firmly retain the tubing 4 in a desired angular orientation and prevent rotation of the tubing 4. (This same advantage is provided by selected shapes of the wires of FIGS. 1–9 as well.)

In one embodiment, the fletching 100 is relatively stiff, so as to slightly stretch the blood vessel and at the particular point of contact create a slight depressed channel in which the fletching rests to anchor the catheter. Preferably, the fletching is not so stiff as to penetrate the wall of the blood vessel but, is sufficiently stiff to prevent excessive undesirable rotation of the tip 8. The upper edge 127 may also be tapered to be thinner in cross section than the lower edge 130 if desired, as explained in more detail with respect to FIGS. 18 and 19 herein.

FIGS. 15 and 16 illustrate an alternative embodiment in which the tip retainer 9 is composed of fletchings 132, 134 and 136 very much like the fletchings on an arrow. That is, as explained specifically with respect to fletching 132, the fletching has a long, tapered region 138, a rounded upper region 140 and a rounded end or tip region 142. Just like the fletching on an arrow, the fletching 132 extends vertically away from the tube 4, perpendicular to the catheter tubing 4, similar to the direction of orientation of fletching 122 of FIG. 14.

In the embodiment of FIG. 15, the fletchings 132, 134, and 136 are spaced a selected distance 137 from the end 120 of the tip portion 8. The rounded upper portion 140 contacts the blood vessel wall spaced a selected distance from the tip portion 8, as illustrated in FIG. 15. In the embodiment of FIG. 16, the fletchings 132, 134 and 136 are positioned such that the rounded upper portion 140 is positioned approximately aligned at the end 120.

An advantage of the embodiment of FIG. 15 is that the flow at the catheter end 120 is not obstructed, interfered or altered by the fletchings 132, 134 and 136. Rather, the blood flow is affected only by the presence of the tip portion 8 which can be configured along conventional lines as known in the art to achieve a desired purpose. The contact to the blood vessel walls by the rounded portion 140 is sufficiently close to the tip portion 8 that the tip portion is retained within the blood flow and is prevented from contacting the blood vessel wall.

On the other hand, in the alternative embodiment of FIG. 16, having the rounded portion 140 approximately aligned with the end 120 provides a firm control exactly at the tip 120 to ensure the maintaining of the tip portion 8 at a fixed location within the blood vessel at all times. The end 120 is exactly anchored in position and undergoes little or no movement because the anchor locations around the blood vessel wall are directly aligned with the tip end 120. This provides a firm positioning system for the tip portion 8 to ensure that the end 120 does not contact the blood vessel wall, even under agitated conditions.

It is contemplated, for example, that in one embodiment a thin wire 139, such as the type shown in FIG. 17A, could be positioned along the tapered edge 138 and along the rounded edge 140 if desired for ensuring that the rounded tip portion 140 always has sufficient spring bias to perform the anchoring function, even in a large blood vessel, and yet have the fletching sufficiently thin for an extended length that it can roll over, providing the improved characteristics of an increased surface contact area if desired.

Figure 17B:
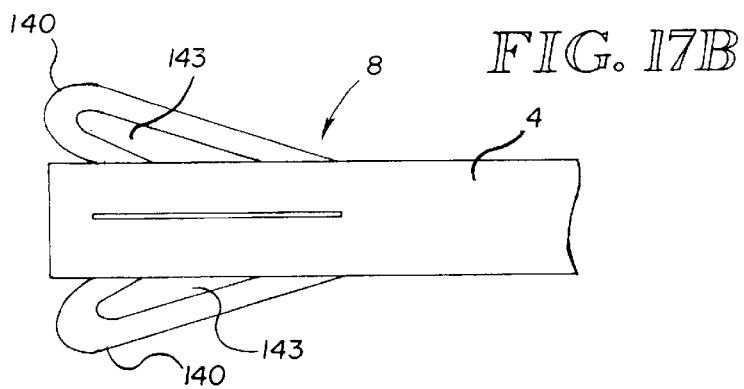
FIG. 17B is a top view of an alternative embodiment of FIG. 17A.

FIG. 17B illustrates a further alternative embodiment for the fletching in which an aperture 143 extends through the fletching. The fletching is thus a ridge of material having a top edge 140. The aperture 143 provides an additional opening for blood flow while the ridges firmly retain the tube 4 within the vessel. The size and shape of the aperture can be varied to alter the spring strength, as desired.

FIGS. 18 and 19 illustrate a particular advantage of the fletching according to the present invention. The fletching is tapered as it extends outward. That is, the fletching is relatively thick at the base 144 where it extends from the tubing 4 and tapers to a very thin edge at the outside regions, particularly at region 140. Having the fletching tapered provides the advantage that one size fletching will fit all blood vessel sizes within a selected range.

For example, as best shown in FIG. 18, the catheter 4 is in a relatively large blood vessel the fletchings 132, 134 and 136 extend straight, and into contact with the blood vessel wall 27. The tip of the fletching 140 may roll over slightly, depending upon the size of the blood vessel. The size of the fletching 132 is selected to ensure that it will at least contact the inner wall 27 of any blood vessel into which it is to be used so that it may perform the tip retaining function as has previously been described. However, in a large blood vessel, such as the type shown in FIG. 18, the tip 140 may slightly contact the edge, thus providing an adequate anchor surface area to retain the catheter tubing 4 in a fixed position as has been described.

FIG. 19 illustrates a smaller blood vessel and the same tip retainer as used in FIG. 18 herein; the fletching is rolled over at the edges, in a broad circumferential contact with the blood vessel wall 27'. The edge 140 can easily roll over and be positioned along the surface of the wall 27' without taking up significant blood vessel area while providing a relatively large contact surface within a small blood vessel. The tapering of the fletching and providing it with thin edges at 140 provides the advantage that even in a small blood vessel, the same fletching may be used except that a larger surface area of the edge portion of the fletching 140 will be in abutting contact with the surface of the wall. This provides the additional advantage of increasing the cross-sectional area of contact between the fletching and the blood vessel, to more securely retain the tip portion 8 within the central region of the blood vessel and prevent contact with the wall 27'.

The tapered fletching provides the additional advantage that a preformed tip assembly 9 can be used in many sizes of blood vessels. A single blood vessel may have a large inner diameter lumen at one region and a small inner diameter lumen in a different region. The difference in diameter may be caused by localized thickening of the walls, injury, fatty build up, or other causes. When the catheter is placed in the vessel, the physician may not be aware of the exact diameter of the blood vessel at the desired location (even though it might be measured ultrasonically, for example). The physician is assured that the catheter tip will be properly retained in the blood flow and spaced from the wall even if the exact dimensions are not as was expected at the installation site. (This advantage is provided in other embodiments also, such as the embodiments of FIGS. 1–9 by the selective withdrawal or extension of the wires, as previously explained.)

Having tapered edges provides another distinct advantage: the relative flexibility and spring bias within the fletching may be easily altered along the fletching as it extends outward. That is, at the very edge of the fletching near rounded portion 140, the resilient bias can be very light because the fletching is very thin at the edges. Closer to the base, the fletching gradually becomes thicker, naturally increasing the spring strength and resilient bias within the fletching. This has the advantage of increasing the centering ability of the tubing 4 because if the tubing begins to be pressed out of position, towards one wall the fletching on that side of the tubing will have the base region pressed closer to the wall; however, the base region being thicker and having a stronger spring action will tend to increase the resilient bias away from the wall and push with more force away from the wall and tend to center the tubing 4 within the blood vessel. Each of the fletchings are constructed with uniform spring bias to act together in generally centering the tubing 4 within the blood vessel and prevent the tubing from becoming too close to the blood vessel wall on any side.

In one embodiment, the spring strength of the fletching varies proportional to the thickness of the fletching. In an alternative embodiment, the fletching is constructed such that the spring bias is not uniform with respect to the thickness of the fletching. For example, a relatively strong spring bias can be placed adjacent the base, even more than would otherwise be present, to ensure that the tubing 4 is always spaced at least a minimum distance from the wall 27. Alternatively, a slightly stronger spring bias may be placed right at the tip 140 than would otherwise be present based on the edges being extremely thin because the edges may be so thin as to have little or no spring bias based on their own thickness. In such an embodiment, the properties of the material or the type of material used may be slightly altered at the very tip region 140 to provide sufficient spring strength to anchor the end even though the tip portions are extremely thin.

FIGS. 18–21 also illustrate alternative embodiments for the orientation of the fletching on the tubing 4. According to one alternative embodiment as shown in FIGS. 18 and 19, the fletching is straight, directly in line with the tubing 4. This is the same style for mounting the fletching on some arrows, as is known in the prior art. Alternatively, the fletching may be mounted at a cant to provide a spiraled fletching as best shown in FIGS. 20 and 21. When the fletching is mounted at a cant, so as to slightly spiral around the tubing 4 this provides the advantageous effect of smoother blood flow through the blood vessel while aiding to maintain the tip 4 in a straight-line orientation with respect to the blood vessel.

The fletching as illustrated in FIGS. 12–21 has the advantage of being easily constructed. In one embodiment, the molding 4 and fletching is constructed as an integral piece by injection molding methods known in the art. The material can be constructed from a polymer, silicone, or any other well-known nonthrombogenic material. Alternatively, the tubing 4 can be extruded with the fletching being provided in an extrusion mold process. Another advantage of the fletching is that it permits easy sheath removal and insertion, as will be explained later in more detail. The fletching also is easily constructed with graduated stiffness along the length of the fletching as it extends away from the tubing 4 providing the advantages previously described.

The insertion and removal of the catheter tubing 4 having the tip retainer on the end thereof will now be explained in particular detail with respect to FIGS. 22–24. The description of FIGS. 22–24 is particularly directed towards an embodiment having loops generally of the type previously described with respect to FIG. 9; however, this is for illustration purposes only and the same or similar method of insertion and removal is uniformly applicable to each of the embodiments described herein.

Referring now to FIG. 22, the catheter 4 having the tip retainer 9 at the end thereof is prepared for introduction into the blood vessel by placing it within an introducer sheath 148. The introducer sheath 148 is preferably made of polyurethane, plastic or some other relatively pliable material that is sufficiently stiff to overcome the spring bias of the retainer member so that the entire assembly has a diameter approximately equal to that of the catheter tubing 4. The introducer sheath 148 includes a handle portion 150 which the physician may use to manipulate the introducer sheath 148 and guide it into the proper position within the blood vessel. In a preferred embodiment, the introducer sheath 148 has a slight taper 152 at the distal end to make the introduction into the blood vessel more simple.

As shown in FIG. 23, the introducer sheath is advanced into the blood vessel 30 until the catheter tube is at the desired location within the blood vessel. At this position, the tip retainer 9 is held within the introducer sheath and does not contact the wall of the blood vessel 30.

As shown in FIG. 24, the introducer sheath 148 is then removed from the catheter tubing 4. According to a preferred embodiment, the introducer sheath 148 is constructed of a relatively thin layer of polyurethane which is easily ripped or torn by the physician. In order to remove the introducer sheath, the physician firmly grabs the handles 150 on either side and begins to tear apart the introducer sheath. The introducer sheath will separate into two pieces, tearing apart outside of the blood vessel and withdrawing the introducer sheath from the catheter tubing 4. As the introducer sheath is withdrawn from the catheter tubing 4, the tip retainer is released and automatically extends outward according to the preset spring bias to contact the blood vessel wall and retain the tip portion 8 at the selected location as has been previously described.

In an alternative embodiment, the sheath is simply removed by sliding it backwards, rather than tearing the sheath into two pieces. As will be appreciated, tearing the sheath into two separate pieces provides the distinct advantage of permitting the introducer sheath to be easily separated from a portion of the tubing without having to completely slide off the end of the tubing outside the body. It also provides the advantage that the physician may easily and uniformly withdraw the introducer sheath while leaving the tubing 4 in the preset position, to permit the tip retainer to be deployed to retain the tip portion 8 in the desired position within the blood vessel.

Removal of the catheter 4 having the tip retainer 9 on the end thereof is easily accomplished with each of the alternative embodiments. In the alternative embodiments of FIGS. 5–21, it will be appreciated that the tip retainer does not penetrate the blood vessel wall 27. Further, in many of these embodiments the tip retainer is constructed to permit easy withdrawal or removal from the blood vessel. According to one method of removal, the catheter 4 is simply withdrawn from the blood vessel, and simultaneously withdraws the tip retainer while in the deployed position. Even though the tip retainer is deployed, such is shown in FIGS. 8 and 9 and others, the orientation is such that the withdrawal may be easily accomplished because the spring bias permits the tip retainer 9 to be pressed inward slightly as necessary. To advance the tip retainer would be difficult, or impossible, because this would serve to increase the spring bias and press the tip retainer 9 more firmly into position against the blood vessel wall, increasing the anchor strength. On the other hand, the withdrawal of the catheter tube 4 tends to pull the tip retainer 9 away from the wall and permit easy removal without excessive stress on the blood vessel wall.

According to an alternative embodiment, the tip retainer is withdrawn from the deployed position so as to not contact the wall by sliding an introducer sheath once more over the tip portion 8 to withdraw the tip retainer 9 from the blood vessel wall. The sheath and catheter tube 4 may then be withdrawn from the blood vessel.

FIGS. 25 and 26 illustrate another preferred embodiment of the tip retainer 9 composed of a loop 168 according to principles of the invention. In the embodiment shown in FIGS. 25 and 26 the tip retainer 9 is comprised of a single loop 168 of wire 166 and silicone tubing 160 having one end 162 and the other end 164 connected to the distal end. Inside the silicone tubing 160 is the stainless steel wire 166. The silicone tubing 160 with the steel wire 166 on the inside thereof form the loop 168, which functions as the tip retainer 9.

The size of the loop 168 is selected based on the size of the blood vessel and position placement of the catheter 4 in that blood vessel. In one embodiment, the loop 168 has a diameter of 20 millimeters and the ends 162 and 164 are connected to the tip portion 8 spaced from the tip portion 8 approximately 7 millimeters. In other alternative embodiments, the diameter of the loop 168 is considerably smaller, in order to be properly sized for placement in the selected vessel of the human body during a kidney dialysis or other procedure, as explained herein.

The ends of the loop 168 are fixed to the catheter 4 by any suitable technique including silicone adhesive, forming an incision in the tubing 4 and insertion into this incision followed by sealing with silicone adhesion, or the like.

The diameter and spring strength of the steel wire 166 is selected to provide the desired spring force to urge the loop 168 to return to the round position as shown in FIG. 25. Generally, a relatively light spring force is acceptable as would be provided small diameter wire 166. Other materials besides stainless steel, such as various alloys of steel, spring steel, teflon coated steel, and the like are also acceptable. The silicone tubing 160 is provided as antithrombogenic coating which is easily manufactured attached to the catheter 4. Any other acceptable antithrombogenic coating besides the silicone tubing 160 could also be used, such as the antithrombogenic coatings described with respect to the other embodiments herein.

In one embodiment, the wire 166 is not present. Instead, only the silicone tubing at 160 is used to form the loop 168 because the proper spring constant is provided from the natural spring within the silicone tubing itself.

FIG. 27 illustrates the tip retainer of FIG. 25 positioned at one possible location within the blood vessel 30 (the tip region 8 must be positioned at a desired location according to the medical procedure being carried out). Preferably, the tip portion 8 is not adjacent a junction 170 between two blood vessels 30 and 30' as shown in FIG. 27. To carry out many medical procedures the tip region 8 must be positioned at a desired location according to the medical procedure being carried out. In some situations, either accidentally or by medical design, the tip region 8 may be adjacent a branch 170 between one blood vessel 30 and another blood vessel 30' to guard against falling into the junction 170, the diameter of the loop 160 is selected to ensure that the tip retainer 9 bridges the junction 170 so that the catheter 4 is anchored within the blood vessel 30 and does not contact the walls of the blood vessels 30 or 30'. Preferably, the diameter of the loop 168 is selected such that when the catheter 4 is compressed within the blood vessel that the longitudinal length of the loop 168 denoted by the distance x in FIG. 27 is longer than the diameter d of a blood vessel which may form a junction with the blood vessel 30'. By selecting a loop sized 168 such that the distance x larger than the diameter of any blood vessel 30' for which a junction 170 is expected to be encountered, the loop can be assured of adequately bridging the blood vessel at the branch 170 and still have sufficient support from the main blood vessel 30 on either side of the walls 27 of the main blood vessel 30. For example, the distance x can be in the range of 1.5 to 3 times the distance d sufficient support along the blood vessel wall 27 from the tip retainer 9 that the tip portion is maintained in a central region of the vessel 30. Of course, the distance x can be significantly longer than three times the diameter d, if desired and depending upon the diameter d which is encountered at various locations within the blood vessel 30. The distance x may be somewhat larger than the diameter of the loop 168 in the round position because as the loop 168 is compressed, the distance x increases to provide an elongated contact position along the length of the wall 27.

The loop 168 is preferably constructed of a small diameter material, such as a silicone tubing having an outside diameter of 1 millimeter or less or a wire having an outside diameter of 0.5 millimeters or less. Using a small diameter material to construct the loop 168 provides the advantage that blood flow through the main blood vessel 30 is not impeded by the tip retaining member 9. If the tip portion 8 happens to be positioned adjacent a junction 170, the additional advantage is that blood flow into or out of the blood vessel 30' that junctions with the blood vessel 30 is not impeded by the loop 168 bridging the junction 170 between the blood vessels. Even if the loop 168 is positioned directly over the opening of 30' at the junction itself, the loop diameter is sufficiently small that blood may easily flow through the blood vessel 30' as needed.

The operation of the device of embodiments 25–27 is as follows. The catheter 4 is positioned in the blood vessel using any acceptable delivery system. The delivery system of the type shown and described with respect to FIGS. 22–24 is acceptable. Upon being positioned within the blood vessel 30, the loop 168 becomes elongated by compression from the walls 27 of the blood vessel 30. The spring constant of the wire 166 is selected to be sufficiently light that the loop 168 is easily compressed by the wall 30 and exerts only a light force upon the inner surface. However, the spring force is sufficiently strong to engage the blood vessel wall 27 and prevent repeated contact between the tip portion 8 and the blood vessel wall 27.

At the conclusion of the medical procedure, the catheter 4 is simply withdrawn by being retracted it while leaving the loop 168 in the deployed position. Alternatively, a retraction sheath may be placed around the catheter 4 which slides along the outer diameter of catheter 4 and compresses the loop 160 to move it away from the wall of the blood vessel similar to that shown in the introduction position of FIG. 23. The catheter 4 is then removed.

FIGS. 28A–28C illustrate alternative embodiments which have been found useful for performing kidney dialysis. Preferably, for kidney dialysis catheter 4 is a double lumen catheter having an inflow lumen 42 and an outflow lumen 44. The tip portions 8 of the lumens are slightly staggered to provide improved inflow and outflow characteristics for kidney dialysis. The attachment locations for ends 162 and 164 (not shown) are selected proximal to the outflow region 42 of one lumen with the loop extending forward, beyond the tip of the in flow lumen 44. FIG. 28A illustrates the embodiment in which the loop 168 is composed only of the silicone 160 and does not include an internal wire 166.

FIGS. 3, 28B and 28C illustrate alternative embodiments for the catheter 4 [double lumen]. FIG. 23 illustrates a double lumen catheter with the lumens ride-by-ride. As shown in FIG. 28B, the catheter 4 can be a double "D" lumen catheter having staggered tip portions for each of the lumens 42 and 44. The walls of the catheter 4 are solid walls formed of any suitable material known in the art. The loop 168 is attached by any acceptable technique, such as silicone adhesive, insertion into the wall of the catheter 4 or the like. FIG. 28C illustrates the embodiment in which the catheter 4 includes additional guideway lumens within the wall of the catheter 4. Specifically, lumens 172 and 174 are provided in a circumferential region of the catheter 4. The lumens extend along the length of the catheter. The loop 168 extends from the lumens 172 and 174, the lumens acting as guideways for the loop 168. The ends of the material that form the loop 168 may extend along the length off the catheter 4 so that the loop 168 may be retracted and extended as necessary. An additional lumen 176 is also provided in the central wall between the two lumens 42 and 44 for additional uses, if desired.

Figure 29:
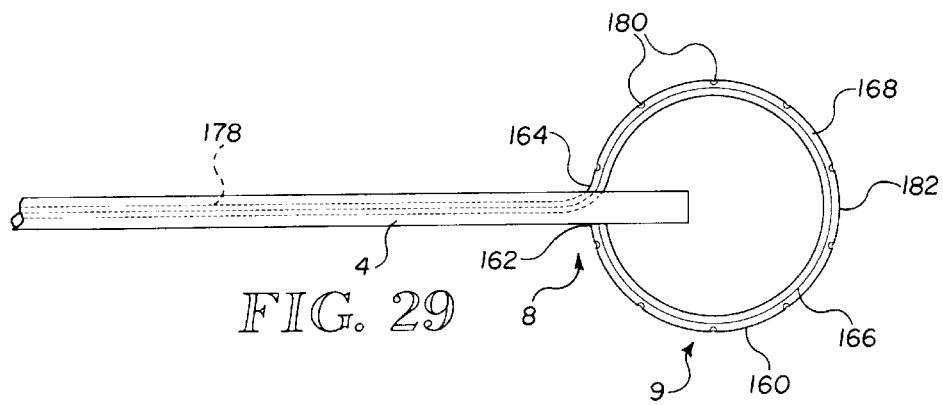
FIG. 29 is an enlarged elevational view of a further alternative embodiment of the tip retainer including a medication delivery system.

FIG. 29 illustrates a still further alternative embodiment instructed according to principles of the present invention. The loop 168 is formed by being rigidly attached at one end 162 to the tip portion 8 and having the other end 164 inserted into a lumen 178 of the catheter 4. In this embodiment, the loop 168 includes a hollow silicone tubing 160 of the type previously described. The wire 166 is within the tubing 160, or alternatively is not used, as desired. The other end of the loop 168 extends into a lumen 178 within the catheter 4. The lumen 178 may be a lumen of the type formed within a wall of the catheter or, alternatively, may be an extension of the silicone tubing 160 connected along the outside of the wall of the catheter 4 or embedded within the wall. In each structure, the lumen 178 provides an open passage way from the tip portion 8 to a proximal portion of the catheter 4, which is external to the patient.

The tubing 160 contains a plurality of apertures 180 spaced from each other around the loop 168. In one embodiment, the apertures 180 are equally spaced from each other around the entire loop. Alternatively, the apertures 180 are positioned only along the side portions of the loop 168, which are anticipated to contact the wall 27 of the blood vessel as shown in FIG. 27. The very tip region 182 of the loop does not contain any apertures in this alternative embodiment.

Medication can then be delivered through the lumen 178, into the loop 168 constructed from the hollow tubing 160 and exit the apertures 180 for administration to the patient. The silicone tube 160 thus becomes a medication delivery system. When the catheter is positioned for an extended time within the human body, as may occur with kidney dialysis, it is known in the art that smooth muscle cell growth, platelet aggregation, and the like to deliver medication may occur. The use of a tip retainer to deliver medication constructed according to principles of the present invention minimizes occlusion of the blood vessel, and reduces destruction of the blood vessel by delivering specific anti-clotting agents to the tip region 8 via the apertures 180 in the loop 168. It is known in the art that the smooth muscle walls surrounding the blood vessel are inhibited from excessive growth by certain medications. One of the problems identified according to principles of the present invention and which the invention seeks to prevent is excessive growth of the smooth muscles around the blood vessel wall which may overgrow into and cause occlusion of the blood vessel 30. The medication delivery system as illustrated in FIG. 29 and described herein advantageously delivers medication precisely to the location desired for inhibiting excessive growth of the muscle cells around the blood vessel wall and for inhibiting platelet aggregation along the wall of the blood vessel or other clotting along the walls of the blood vessel. The medications which may delivered include TPA, an anticlotting agent; strepokinase, heparin, hirudin, or the like. In some instances, clotting beings to occur along the walls 27 of the blood vessel 30. The loop 168 is in actual contact with the blood vessel wall 27. The medication can therefore be delivered directly to the wall of the blood vessel with benefits obtained in addition to those which may be obtained by delivering the same medication exiting from the main lumen 28 of the catheter.

The position, size and relative location of the apertures 180 are selected to provide the desired delivery medication. In some embodiments, having the apertures 180 spaced equidistance from each other and opening to both the inside and outside of the loop 168 is desirable to provide medication equally around the loop 168. In an alternative embodiment, the apertures 180 are spaced only on an outside surface of the loop 168 to deliver the medication outward from the loop. In a further alternative embodiment, the apertures 180 are positioned only at or near locations which are anticipated to come in contact with the wall 27 of the blood vessel 30. The apertures 180 may be oriented to discharge the medication along the surface of the blood vessel wall 27 and thus are radially offset from the outside position to deliver the medication adjacent the wall 27 so that the wall 27 does not block outflow of the medication.

Having the tubing 160 or, alternatively, a wire 166 within the tubing 160 extend to the proximal end of the catheter 4 provides the additional advantage that the loop 168 may be retracted or extended as necessary. When the catheter 4 is inserted into the patient, the loop 168 can be in a retracted, small diameter position held tightly against the tip portion 8. Once the catheter is at the proper location, the wire 166, if present, or alternatively the tubing 160, may be pushed along the lumen 178 to enlarge the loop 168 to a size and shape as described with respect to FIG. 27. The loop 168 thereafter remains in the extended position during the medical procedure. At the conclusion of the medical procedure, the wire 166, or alternatively the lumen 160, are retracted down the lumen 178 to again reduce the diameter of the loop 168. The loop 168 may also be retracted or extended using the lumens 172 and 174 of the catheter of FIG. 28C. The catheter 4 is then withdrawn from the patient. Alternatively, a delivery system of the type described with respect to FIGS. 22–24 may be used and the loop 168 starting in the deployed position and only being retracted for removal of the catheter 4.

Figure 30:
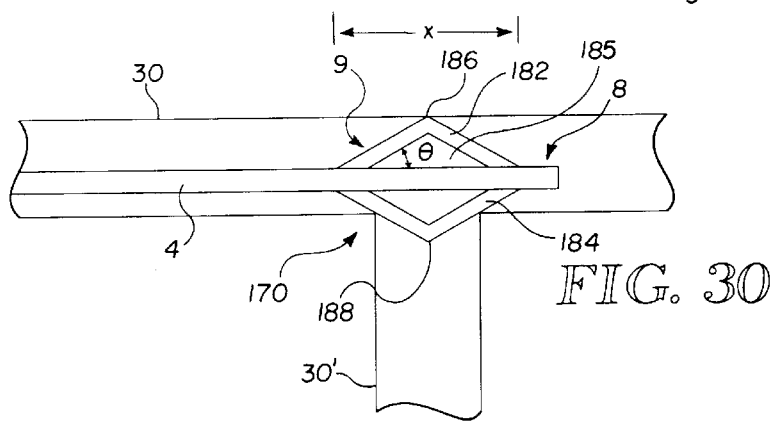
FIG. 30 is a side elevational view of a further alternative embodiment positioned at a possible location within the blood vessel.

FIG. 30 illustrates a further alternative embodiment of the tip retainer 9. According to the embodiment of FIG. 30, two triangular silicone strips 182 and 184 are positioned adjacent the tip portion 8. The length x of the silicone strips 182 for combination with the angle θ with respect to the wall of the catheter 4 are selected to cause the respective tip regions 186 and 188 to contact the walls of the blood vessel 30 with light spring force to anchor the tip portion 8 to the blood vessel 30. The angle θ is also selected to be sufficiently small that if the tip portion 8 happens to be positioned adjacent a junction 170 that the sides of the triangular member contact the walls 27 at either edge of the junction 170 and prevent the tip portion 8 from becoming sufficiently close to the wall adjacent the junction that it contacts the junction itself or the wall adjacent junction. In the event one of the triangular members 184 enters the blood vessel 301 at junction 170, two contact points are advantageously provided instead of the single previous point 188, thus further increasing the stability of the anchoring of the tip portion 8. The number of triangular members 182, 184 used depends on the particular application, and preferably 2, 3 or 4 such triangular members are used.

The triangular members 182 and 184 include respective apertures 185. The apertures 185 advantageously permit the spring constant of the triangular members 182 to be selected by making the aperture small or large to provide a correspondingly large or small spring constant as desired. Further, the apertures may also provide the benefit of the triangular members 182 and 184 minimizing interference with the flow of blood.

Constructing the triangular members 182, 184 from a strip of silicone provides the advantage previously described with respect to the loop 168 that blood flow through the blood vessels 30 or 30' is not impeded with the catheter 4 in position. Flow to or from the branch at the junction is not restricted.

Figure 31:
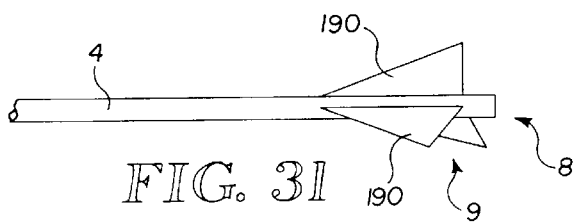
FIG. 31 is an enlarged elevational view of a further alternative embodiment of the tip retainer.
Figure 32:
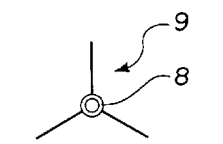
FIG. 32 is an end view of the embodiment of FIG. 31.

FIG. 31 illustrates an alternative embodiment for the tip retaining member 9 comprised of triangular members 190 constructed from sheets of silicone. Preferably, the sheets are solid sheets of silicone which are relatively thin, less than 1 millimeter, so as to not impede the blood flow and yet be sufficiently strong to retain the catheter 4 anchored in a space position from the blood vessel wall 27.

Figure 33A:
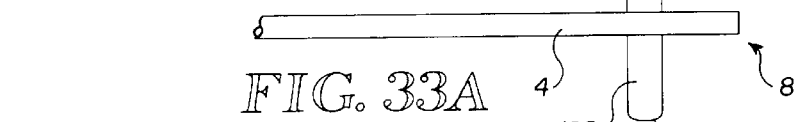
FIG. 33A is a side elevational view of a further alternative embodiment of the tip retainer.
Figure 33B:
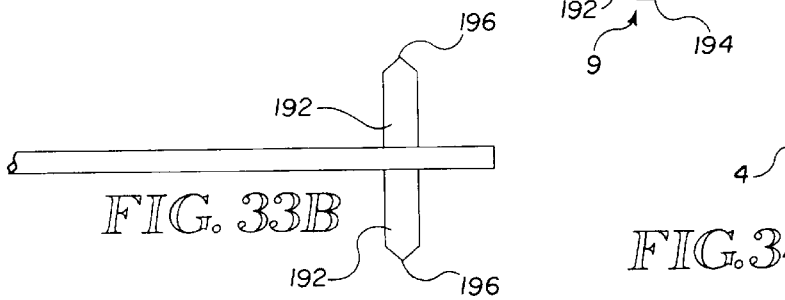
FIG. 33B is a further alternative embodiment of the tip retainer of FIG. 33A.
Figure 34:
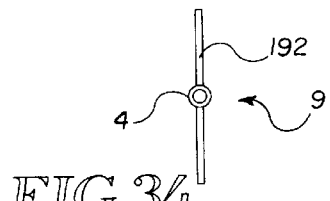
FIG. 34 is an end view of the tip retainer of FIGS. 33A and 33B.

FIGS. 33A, 33B and 34 illustrate an alternative embodiment for a tip retainer in the form of longitudinal strips 192 of silicone sheeting. In the embodiment of FIG. 33A, the tips 194 are rounded to reduce the trauma in the blood vessel and spread the spring force over a greater area in the blood vessel. In the alternative embodiment of FIG. 33B, the tip portions 196 are pointed to concentrate the spring forces at a single location and slightly deflect the wall 27 of the blood vessel at the point of contact 196. Having a more pointed tip 196 increases the force with which the tip member 9 is embedded into the wall 27 of the blood vessel and may be desired in some embodiments. In the embodiments shown in FIGS. 33A, 33B and 34 two strips 192 of silicone sheeting are shown. However, it is contemplated that three or four strips may also be used spaced equidistance around the catheter 4 similar to that shown in FIGS. 12–21, if desired.

Figure 35:
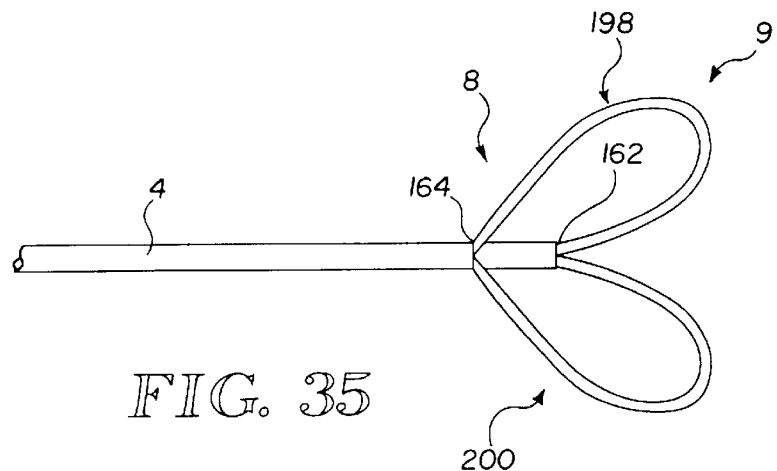
FIG. 35 is a top plan view of a further alternative embodiment of the tip retainer mounted on an alternative embodiment of the catheter.
Figure 36:
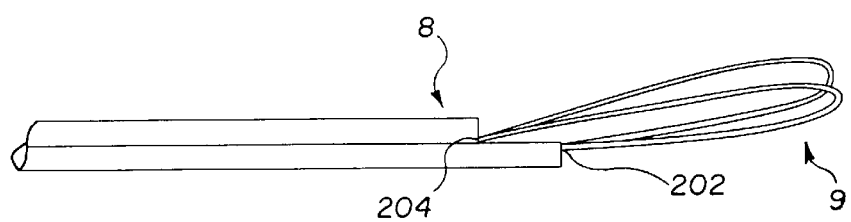
FIG. 36 is a side elevational view of the embodiment of FIG. 35.

FIGS. 35 and 36 illustrate an alternative embodiment for the tip retainer 9 composed of two loops 198 and 200. The embodiment of FIGS. 35 and 36 is particularly adapted to use on a catheter for having a double lumen with the opening staggered as illustrated in FIGS. 36 and 28A. According to this embodiment, a first end 162 of each loop originates near the upper region 202 of the most forward tip of the catheter 4, extends outward, in a loop of the desired shape, and terminates at the base region 204 of the opening of the other lumen where the other end 164 is attached. The loops 198 and 200 are constructed from silicone tubing, silicone sheeting or alternatively, from a tubing having a spring wire therein of the type previously described with respect to FIGS. 25–27. The use of loops or loop having their terminated ends 162 and 164 spaced longitudinally along the catheter may be used in the other embodiments of FIGS. 25–29 and is desired in some medical procedures to provide increased stability at different points along the tip portion 8 of the catheter 4.

Figure 37:
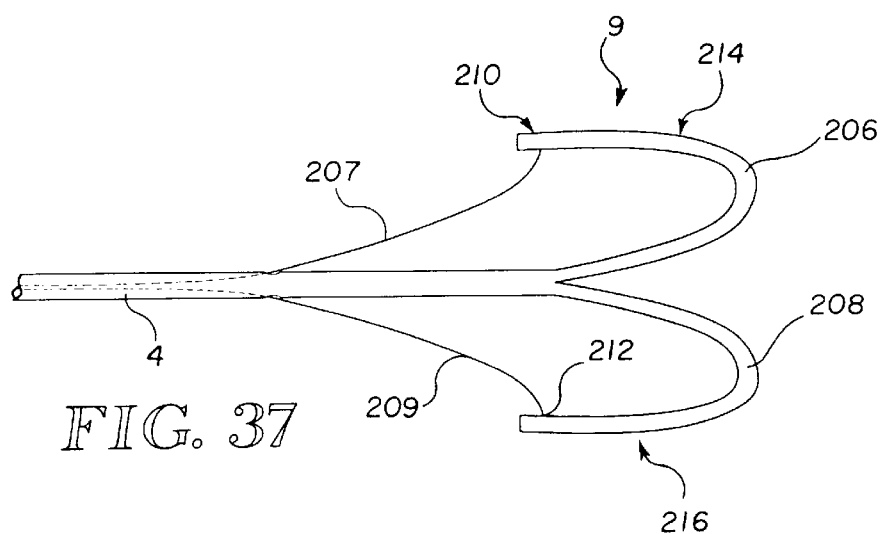
FIG. 37 is a side elevational view of a further alternative embodiment of the tip retainer.

FIG. 37 illustrates an alternative embodiment in which the catheter itself is modified to provide the tip retaining member 9. In this embodiment, the tip portion of the catheter 4 is severed by an incision along the tip for a selected distance creating two halves, 206 and 208. A string, wire or other attachment device is connected to the ends 210 and 212 respectively of the halves 206 and 208. The strings 207 and 209 are then retracted a desired amount to form two loops 214 and 216 in the end of the catheter 4 similar to that shown in the embodiment of FIGS. 35 and 36. The attaching members 207 and 209 are retracted the desired amount to form the loops 214 and 216 of a selected size and shape. A slight retraction of the attachment means 207 and 209 will cause the loops 214 and 216 to be relatively large and extend into solid abutting contact with the walls of the blood vessel. If the loop catheter 4 is positioned in a smaller portion of the blood vessel, the attachment members 207 and 209 can be further withdrawn, decreasing the size of the loops 214 and 216 to provide the desired spring bias force for retaining the tip portion 8 within the blood vessel 30. The embodiment of FIG. 37 provides the advantage of ease of manufacture because the catheter itself is modified to form the tip retaining member 9. Alternative to using wires 207 and 209, if the size of the loops 214 and 216 is previously known, the tip portions 210 and 212 may be attached to the side wall of the lumen 4 by the appropriate adhesive to easily form the loops 214 and 216 having a desired size and spring constant. For this embodiment, the attachment wires 207 and 209 are not necessary and loops similar to that shown in FIG. 35 can easily be formed by sacrificing a portion of the tip region of the catheter itself and using a catheter material to form the loops 214 and 216.

Figure 38A:
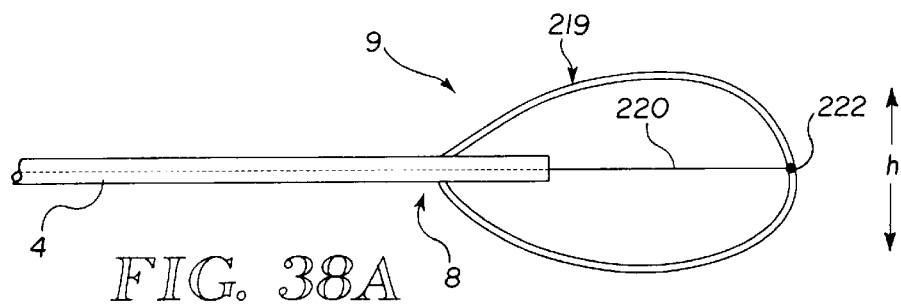
FIG. 38A is a side elevational view of a further alternative embodiment the tip retainer in an extended position for insertion.
Figure 38B:
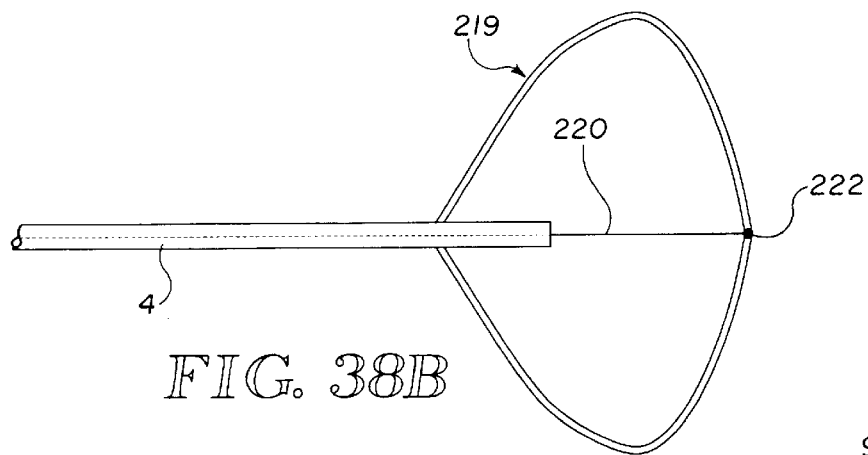

FIGS. 38A and 38B illustrate an alternative embodiment for the tip retainer 9. A loop 219 constructed from any acceptable material having the desired spring constant is attached to the tip region 8 of the catheter for using any one of the acceptable techniques described herein. In addition, a retraction wire 220 is attached adjacent a tip region 222 of the loop 219. The retraction wire 220 extends along the catheter 4, either along the outside surface or through a lumen in its position near the proximal end for manipulation by a physician. The loop 219 is formed with the shape such that the spring memory forces if into an extended, elongated position while relaxed, such as shown in FIG. 38A. Preferably, the loop 219 in the relaxed position will have a height h approximately equal to that of the catheter for itself. After the catheter 4 is advanced to the desired position of the blood vessel 30, the retraction wire 220 is retracted by the physician causing the loop 219 to go outward and engage in abutting contact with the walls 27 of the blood vessel 30. The retraction line 220 is then secured at a proximal end in the catheter 4, outside the patient, and acts as a tip retainer deployment device to maintain the tip portion 8 of the catheter 4 within the blood vessel. At the conclusion of the medical procedure, retraction line 220 is released which permits the wire 219 to return to its relaxed position as shown in FIG. 38A. The catheter 4 is then removed from the blood vessel. The loop 219 may be composed of a single loop of material of the type shown in FIGS. 25–27, or alternatively, may be composed of two or more loops in the form of an egg beater type pattern to provide multiple abutting contact points with the wall of the blood vessel when the retraction wire 220 is retracted.

Figure 39:
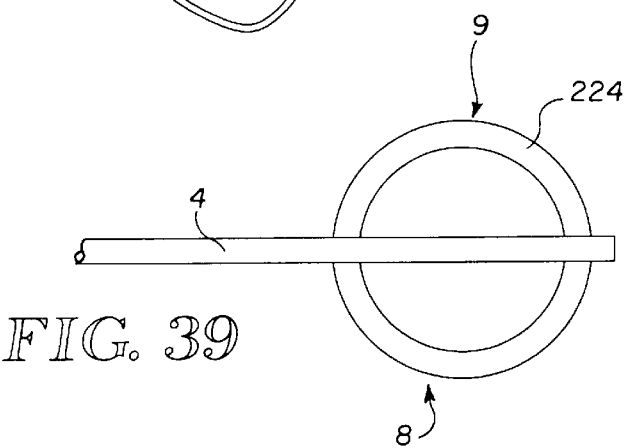
FIG. 39 is a side elevational view of a further alternative embodiment of the tip retainer.

FIG. 39 illustrates a further alternative embodiment at the tip retainer 9 in which a circle 224 of silicone sheeting is affixed near the distal end 8 of the catheter 4 to form the tip retainer 9. The loop 224 provides extended contact points with the blood vessel wall along its entire length similar to that shown for the loop of FIG. 27. In the embodiment of FIG. 39, the loop 224 is positioned with its most forward end adjacent the tip portion 8 and extending backwards, while in the embodiment of FIG. 27, the loop 168 extends forward from the tip portion 8. Similar to the embodiment shown and described with respect to FIGS. 25–27, the loop 224 may be composed of flat silicone sheeting, hollow silicone tubing having a spring wire therein, or alternatively a spring wire by itself coated with an antithrombogenic material.

Figure 40:
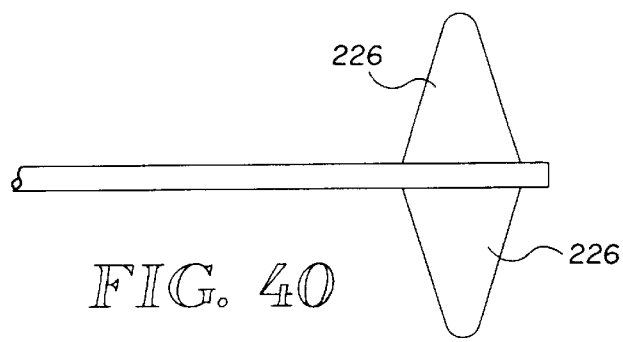
FIG. 40 is a side elevational view of a further alternative embodiment of the tip retainer.

FIG. 40 illustrates a further alternative embodiment at the tip retainer member 9 according to the present invention which includes vanes 226 having a generally triangular shape. The shape of the vanes 226 are slightly different from the shape of the vanes 192 because they extend in a triangular shape from the catheter wall 4. The broader, triangular base of the vanes 226 advantageously permits the strength of the vein 226, and thus the spring constant to gradually increase towards the body of the catheter 4 while maintaining the same thickness for the vein 226 as shown in FIG. 34. The particular shape of the triangle 226 is selected depending upon the desired location within the blood vessel to provide the spring constant which maintains the catheter 4 at a spaced position from the blood vessel wall at all times, even as may occur from repeated movement of the patient.

While the preferred embodiment of the invention has been illustrated and described, it will be appreciated that various changes can be made therein without departing from the spirit and scope of the invention.

What is claimed is:

1. A catheter adapted for insertion into a blood vessel having blood flowing therethrough, comprising:

a catheter having a distal end, a proximal end, a tip and an internal passageway for permitting fluids to pass through the catheter; and a tip immobilizing means located at the distal end of the catheter for anchoring the distal end of the catheter within the blood flow to maintain the tip of the catheter in a spaced relationship from a blood vessel wall and to prevent the tip of the catheter from contacting a wall of the blood vessel without substantially obstructing fluid flow of blood through the blood vessel, such that catheter failure due to stenosis or thrombosis at the catheter distal end if reduced.

2. A catheter adapted for insertion into a blood vessel comprising:

a catheter having a lumen therein that permits fluids to pass through said catheter, the catheter having a tip portion and a proximal portion spaced form the tip portion;

a tip retainer assembly attached to the tip portion of the catheter; and a plurality of wall contact members, each of which contacts a blood vessel wall when the catheter is within a blood vessel, the wall contact members being a part of the tip retainer assembly, the wall contact members including a wall contact portion for contacting the blood vessel wall at a selected location and remaining in contact with the blood vessel wall for an extended time, the wall contact members being attached to said catheter tip portion and maintaining the catheter tip a spaced distance from the blood vessel wall and preventing the catheter tip from contacting the blood vessel to prevent damage to the blood vessel wall by repeated contact between the catheter tip and the blood vessel wall.

3. The catheter according to claim 2 wherein each of said wall contact members is spring biased with a selected spring force for extending into abutting contact with said blood vessel wall, each of said wall contact members being spaced from each other circumferentially around the catheter tip portion to provide a tip retainer assembly that resiliently biases the catheter tip a fixed distance spaced from said blood vessel wall and maintains the catheter tip within the blood flow region.

4. The catheter according to claim 2 wherein said wall contact portion contacts said wall at a position adjacent the tip of said catheter tip.

5. The catheter according to claim 2 wherein said wall contact members are spring biased for permitting the tip portion to move within the blood vessel for providing a spring bias force that prevents repeated contact between the tip portion and the blood vessel wall to prevent damage to the blood vessel wall.

6. The catheter according to claim 5 wherein the wall contact members exert a light spring force for centering the tip portion within the blood vessel wall when the tip portion is approximately in the center of the blood vessel and exerts a gradually increasing spring bias force as the tip portion becomes closer to the wall, increasing the force with which the catheter tip portion is held away from the wall as the tip portion comes closer to the wall, the light spring force permitting relative movement of the catheter tip, and the gradually increasing spring force making it more difficult for the catheter tip to actually contact the wall.

7. An assembly adapted for insertion into a blood vessel comprising:

a catheter means for introduction into a blood vessel, the catheter means being adapted to being positioned within the blood vessel, the catheter means having a tip portion;

an introducer assembly means for aid in inserting the said catheter means into a blood vessel; and a tip retainer assembly means located at the distal end of the catheter for retaining the tip portion in a relatively fixed position within a blood vessel, the tip retainer assembly means being adapted to be in a retracted position when the catheter means is not positioned within the blood vessel and in a deployed position when the catheter means is within the blood vessel, the tip retainer assembly means retaining the tip portion of the catheter means in a spaced position from the blood vessel wall and preventing repeated contact of the tip portion of the catheter means with the blood vessel wall.

8. The assembly according to claim 7 wherein the introducer assembly includes a means for holding the blood vessel open to facilitate positioning of the catheter means at a desired location in the blood vessel.

9. The assembly according to claim 8 wherein said means for holding the blood vessel open includes an introducer sheath means for enclosing the catheter means and for holding the blood vessel open.

10. The assembly according to claim 9 wherein said introducer sheath means includes an introducer sheath removal means for permitting easy removal of the introducer sheath from the catheter means.

11. The assembly according to claim 10 wherein the introducer sheath removal means includes a tearable membrane which forms a tubular portion of the introducer sheath for enclosing the catheter means and gripping means for gripping the introducer sheath, while tearing the introducer sheath to the introducer sheath from the catheter means.

12. The assembly according to claim 7 wherein said tip retainer assembly means includes a spring means for permitting the tip portion to move a limited distance within the blood vessel but for providing a spring bias force that prevents repeated contact between the tip portion and the blood vessel wall to prevent damage to the blood vessel wall.

13. The assembly according to claim 12 wherein the spring force provided by the spring means increases in strength as the tip portion becomes closer to the blood vessel wall, thus serving to maintain a spaced relationship between the blood vessel wall and the tip portion.

14. The assembly according to claim 12 wherein the spring means exerts a light spring force for centering the tip portion within the blood vessel wall and exerts a gradually increasing spring force as the tip portion becomes closer to one wall, increasing the force with which the catheter tip portion is held away from the wall as the tip portion comes closer to the wall, the light spring force permitting some relative movement of the catheter tip, and the gradually increasing spring force making it more difficult for the catheter tip to actually contact the wall.

15. A method of inserting a catheter having a tip retainer assembly attached at one end thereof into a blood vessel, comprising:

placing a sheath insertion tube assembly within a blood vessel, the sheath insertion tube assembly including an insertion sheath having handles at a proximal end thereof which are not inserted into the blood vessel, a tip portion which is inserted into a blood vessel and a catheter within the insertion sheath, said catheter having a tip retainer assembly at a distal end of said catheter;

maneuvering the insertion sheath assembly with the catheter therein to a selected position within the blood vessel; and withdrawing the insertion sheath from the catheter tube while maintaining the catheter tube at a fixed position within the blood vessel, the withdrawal of the insertion sheath causing the tip retainer assembly to be deployed in a spaced position away from the catheter tube such that the tip retainer assembly contacts the blood vessel wall with a preselected resilient spring biased force and maintains the catheter tip anchored at a preselected location and held a selected distance from the blood vessel wall to prevent the catheter tip from contacting the blood vessel wall.

16. The method according to claim 15 wherein said tip retainer assembly includes a plurality of wires, the method further including:

selectively extending or retracting said plurality of wires at a distal region of the tip retainer to ensure that the tip retainer assembly contacts the blood vessel wall with sufficient force to retain the tip spaced from the wall but not with excessive force such as to significantly distort the blood vessel wall shape or penetrate through the wall.

17. The method of securing a catheter tip at a selected location in a blood vessel, comprising:

inserting a catheter within a blood vessel, the catheter having a tip and a tip retainer assembly adjacent the tip in a retracted position, the tip retainer assembly having a distal end in a retracted position and including a control assembly at a proximal end of the catheter outside the blood vessel;

maneuvering the catheter tip to a selected location within the blood vessel; and manipulating the control assembly of the tip retainer to deploy the tip retainer assembly into abutting contact with the blood vessel wall such that the tip retainer assembly contacts the blood vessel wall with sufficient force to maintain the catheter tip anchored at a preselected location and holds the catheter tip in a spaced relationship from the blood vessel wall to prevent the catheter tip from repeatedly contacting the blood vessel wall.

\* \* \* \* \*

UNITED STATES PATENT AND TRADEMARK OFFICE
CERTIFICATE OF CORRECTION

PATENT NO : 6,071,263
DATED : Jun. 6, 2000
INVENTOR(S) : Thomas R. Kirkman

It is certified that errors appear in the above-identified patent and that said Letters Patent are hereby corrected as shown below:

Claim 2, column 25, line 46, "spaced form the tip" should read --spaced from the tip--.

Claim 11, column 26, line 63, "sheath to the introducer" should read --sheath to remove the introducer--.

Signed and Sealed this

Twenty-seventh Day of March, 2001

*Attest:*

NICHOLAS P. GODICI

*Attesting Officer*  *Acting Director of the United States Patent and Trademark Office*

UNITED STATES PATENT AND TRADEMARK OFFICE
CERTIFICATE OF CORRECTION

PATENT NO. : 6,071,263
DATED : June 6, 2000
INVENTOR(S) : Thomas R. Kirkman

It is certified that error appears in the above-identified patent and that said Letters Patent is hereby corrected as shown below:

<u>Claim 1, column 25,</u>
Line 41, "end if reduced" should read -- end is reduced --.

Signed and Sealed this

Ninth Day of October, 2001

*Attest:*

*Attesting Officer*

NICHOLAS P. GODICI
*Acting Director of the United States Patent and Trademark Office*